(12) United States Patent
McIntosh

(10) Patent No.: US 7,387,997 B2
(45) Date of Patent: Jun. 17, 2008

(54) α-CONOTOXIN MII ANALOGUES

(75) Inventor: J. Michael McIntosh, Salt Lake City, UT (US)

(73) Assignee: University of Utah, Salt Lake City, UT (US)

( * ) Notice: Subject to any disclaimer, the term of this patent is extended or adjusted under 35 U.S.C. 154(b) by 0 days.

(21) Appl. No.: 11/269,879

(22) Filed: Nov. 9, 2005

(65) Prior Publication Data

US 2006/0211623 A1 Sep. 21, 2006

Related U.S. Application Data

(60) Provisional application No. 60/625,945, filed on Nov. 9, 2004.

(51) Int. Cl.
*A61K 38/10* (2006.01)
*C07K 7/00* (2006.01)
*C07K 7/08* (2006.01)

(52) U.S. Cl. .......................... 514/13; 530/326; 530/857

(58) Field of Classification Search .................. 514/13; 530/326, 857
See application file for complete search history.

(56) References Cited

U.S. PATENT DOCUMENTS 4,447,356 A 5/1984 Olivera et al.
5,514,774 A 5/1996 Olivera et al.
5,780,433 A 7/1998 McIntosh et al.

FOREIGN PATENT DOCUMENTS

WO    WO 9511256 A1 *  4/1995

OTHER PUBLICATIONS

Result 2, Geneseq database search, alignment of SEQ ID No. 8 with SEQ ID No. 19 of Olivera et al., WO 95/11256 A1, search performed on May 24, 2007.*
Cartier, G.E. et al. (1996). A new α-conotoxin which targets α3β2 nicotinic acetylcholine receptors. *J Biol Chem* 271(13): 7522-7528.
McIntosh, J. M. et al., Conus Peptides as Probes for Ion Channels, (1998). *Methods Enzymol*. 294:605-624.
Olivera, B.M. et al., Peptide Neurotoxins from Fish-Hunting Cone Snails (1985) *Science* 230:1338-1343.
Olivera, B.M. et al., Diversity of *Conus* Neuropeptides, (1990) *Science* 249:257-263.
Shon, K. et al. (1997). Three-dimensional solution structure of α-conotoxin MII, an α3β2 neuronal nicotinic acetylcholine receptor-targeted ligand. *Biochemistry* 36: 15693-15700.

* cited by examiner

*Primary Examiner*—Rebecca E. Prouty
*Assistant Examiner*—Rosanne Kosson
(74) *Attorney, Agent, or Firm*—Rothwell, Figg, Ernst & Manbeck P.C.

(57) ABSTRACT

The invention relates to novel conopeptides and/or novel Luses of conopeptides. The conopeptides of the invention are analogs of α-Conotoxin MII that are selective for α6-containing nAChRs as described herein.

3 Claims, 6 Drawing Sheets

Fig. 2A
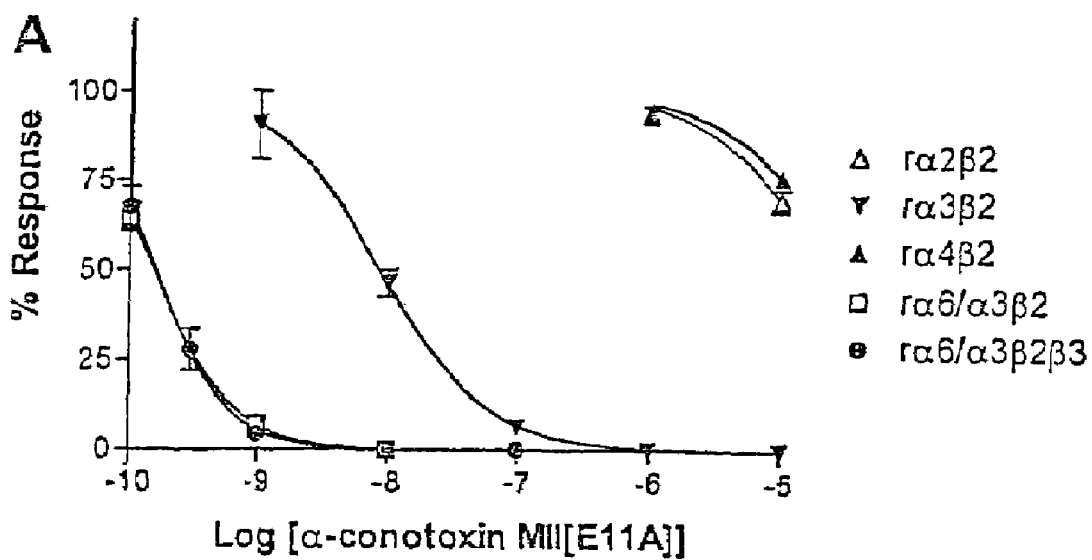
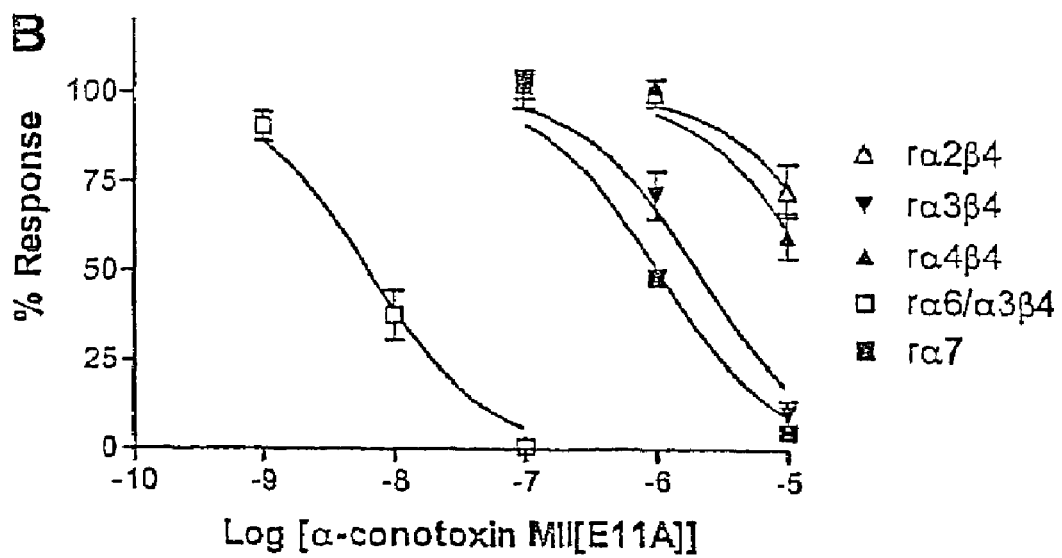
Fig. 2B

SEQUENCE LISTING

<160> NUMBER OF SEQ ID NOS: 16

<210> SEQ ID NO 1
<211> LENGTH: 16
<212> TYPE: PRT
<213> ORGANISM: Conus magus

<400> SEQUENCE: 1

Gly Cys Cys Ser Asn Pro Val Cys His Leu Glu His Ser Asn Leu Cys
1               5                   10                  15

<210> SEQ ID NO 2
<211> LENGTH: 16
<212> TYPE: PRT
<213> ORGANISM: Conus magus

<400> SEQUENCE: 2

Gly Cys Cys Ala Asn Pro Val Cys His Leu Glu His Ser Asn Leu Cys
1               5                   10                  15

<210> SEQ ID NO 3
<211> LENGTH: 16
<212> TYPE: PRT
<213> ORGANISM: Conus magus

<400> SEQUENCE: 3

Gly Cys Cys Ser Ala Pro Val Cys His Leu Glu His Ser Asn Leu Cys
1               5                   10                  15

<210> SEQ ID NO 4
<211> LENGTH: 16
<212> TYPE: PRT
<213> ORGANISM: Conus magus

<400> SEQUENCE: 4

Gly Cys Cys Ser Asn Ala Val Cys His Leu Glu His Ser Asn Leu Cys
1               5                   10                  15

<210> SEQ ID NO 5
<211> LENGTH: 16
<212> TYPE: PRT
<213> ORGANISM: Conus magus

<400> SEQUENCE: 5

Gly Cys Cys Ser Asn Pro Ala Cys His Leu Glu His Ser Asn Leu Cys
1               5                   10                  15

<210> SEQ ID NO 6
<211> LENGTH: 16
<212> TYPE: PRT
<213> ORGANISM: Conus magus

<400> SEQUENCE: 6

Gly Cys Cys Ser Asn Pro Val Cys Ala Leu Glu His Ser Asn Leu Cys
1               5                   10                  15

<210> SEQ ID NO 7
<211> LENGTH: 16
<212> TYPE: PRT
<213> ORGANISM: Conus magus

<400> SEQUENCE: 7

Gly Cys Cys Ser Asn Pro Val Cys His Ala Glu His Ser Asn Leu Cys

```
                1               5                  10                  15
```

<210> SEQ ID NO 8
<211> LENGTH: 16
<212> TYPE: PRT
<213> ORGANISM: Conus magus

<400> SEQUENCE: 8

```
Gly Cys Cys Ser Asn Pro Val Cys His Leu Ala His Ser Asn Leu Cys
1               5                  10                  15
```

<210> SEQ ID NO 9
<211> LENGTH: 16
<212> TYPE: PRT
<213> ORGANISM: Conus magus

<400> SEQUENCE: 9

```
Gly Cys Cys Ser Asn Pro Val Cys His Leu Glu Ala Ser Asn Leu Cys
1               5                  10                  15
```

<210> SEQ ID NO 10
<211> LENGTH: 16
<212> TYPE: PRT
<213> ORGANISM: Conus magus

<400> SEQUENCE: 10

```
Gly Cys Cys Ser Asn Pro Val Cys His Leu Glu His Ala Asn Leu Cys
1               5                  10                  15
```

<210> SEQ ID NO 11
<211> LENGTH: 16
<212> TYPE: PRT
<213> ORGANISM: Conus magus

<400> SEQUENCE: 11

```
Gly Cys Cys Ser Asn Pro Val Cys His Leu Glu His Ser Ala Leu Cys
1               5                  10                  15
```

<210> SEQ ID NO 12
<211> LENGTH: 16
<212> TYPE: PRT
<213> ORGANISM: Conus magus

<400> SEQUENCE: 12

```
Gly Cys Cys Ser Asn Pro Val Cys His Leu Glu His Ser Asn Ala Cys
1               5                  10                  15
```

<210> SEQ ID NO 13
<211> LENGTH: 16
<212> TYPE: PRT
<213> ORGANISM: Conus magus

<400> SEQUENCE: 13

```
Gly Cys Cys Ser Asn Pro Val Cys Ala Leu Glu His Ser Asn Ala Cys
1               5                  10                  15
```

<210> SEQ ID NO 14
<211> LENGTH: 16
<212> TYPE: PRT
<213> ORGANISM: Conus magus

<400> SEQUENCE: 14

```
Gly Cys Cys Ser Asn Pro Val Cys His Ala Glu His Ser Asn Ala Cys
1               5                  10                  15
```

```
<210> SEQ ID NO 15
<211> LENGTH: 16
<212> TYPE: PRT
<213> ORGANISM: Conus magus

<400> SEQUENCE: 15

Gly Cys Cys Ser Asn Pro Val Cys His Leu Ala His Ser Asn Ala Cys
1               5                   10                  15

<210> SEQ ID NO 16
<211> LENGTH: 16
<212> TYPE: PRT
<213> ORGANISM: Conus magus

<400> SEQUENCE: 16

Gly Cys Cys Ala Asn Pro Val Cys Ala Leu Glu His Ser Asn Leu Cys
1               5                   10                  15
```

α-CONOTOXIN MII ANALOGUES

CROSS-REFERENCE TO RELATED APPLICATION

The present application is claims the benefit of and priority under 35 U.S.C. § 119(e) to U.S. Provisional Patent Application Ser. No. 60/625,945, filed 9 Nov. 2004, incorporated herein by reference.

This invention was made with Government support under Grants No. GM48677, MH53631, DA12242 and NS11323, awarded by the National Institute of General Medical Sciences, National Institutes of Health, Bethesda, Md. The United States Government has certain rights in the invention.

BACKGROUND OF THE INVENTION

The invention relates to novel conopeptides and/or novel uses of conopeptides as described herein. More specifically, the present invention is directed to the conopeptide α-conotoxin MII analogs (α-MII) as described herein that are selective for α6-containing nicotinic acetylcholine receptors.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

*Conus* is a genus of predatory marine gastropods (snails) which envenomate their prey. Venomous cone snails use a highly developed projectile apparatus to deliver their cocktail of toxic conotoxins (also referred to as conopeptides herein) into their prey. In fish-eating species such as *Conus magus* the cone detects the presence of the fish using chemosensors in its siphon and when close enough extends its proboscis and fires a hollow harpoon-like tooth containing venom into the fish. The venom immobilizes the fish and enables the cone snail to wind it into its mouth via an attached filament. For general information on *Conus* and their venom see the website address http://grimwade.biochem.unimelb.edu.au/cone/referenc.html. Prey capture is accomplished through a sophisticated arsenal of peptides which target specific ion channel and receptor subtypes. Each *Conus* species venom appears to contain a unique set of 50-200 peptides. The composition of the venom differs greatly between species and between individual snails within each species, each optimally evolved to paralyse it's prey. The active components of the venom are small peptides toxins, typically 12-30 amino acid residues in length and are typically highly constrained peptides due to their high density of disulphide bonds.

The venoms consist of a large number of different peptide components that when separated exhibit a range of biological activities: when injected into mice they elicit a range of physiological responses from shaking to depression. The paralytic components of the venom that have been the focus of recent investigation are the α-, ω- and μ-conotoxins. All of these conotoxins act by preventing neuronal communication, but each targets a different aspect of the process to achieve this. The α-conotoxins target nicotinic ligand gated channels, the μ-conotoxins target the voltage-gated sodium channels and the ω-conotoxins target the voltage-gated calcium channels (Olivera et al., 1985; Olivera et al., 1990). For example a linkage has been established between α-, αA- & φ-conotoxins and the nicotinic ligand-gated ion channel; ω-conotoxins and the voltage-gated calcium channel; μ-conotoxins and the voltage-gated sodium channel; δ-conotoxins and the voltage-gated sodium channel; κ-conotoxins and the voltage-gated potassium channel; conantokins and the ligand-gated glutamate (NMDA) channel.

However, the structure and function of only a small minority of these peptides have been determined to date. For peptides where function has been determined, three classes of targets have been elucidated: voltage-gated ion channels; ligand-gated ion channels, and G-protein-linked receptors.

*Conus* peptides which target voltage-gated ion channels include those that delay the inactivation of sodium channels, as well as blockers specific for sodium channels, calcium channels and potassium channels. Peptides that target ligand-gated ion channels include antagonists of NMDA and serotonin receptors, as well as competitive and noncompetitive nicotinic receptor antagonists. Peptides which act on G-protein receptors include neurotensin and vasopressin receptor agonists. The unprecedented pharmaceutical selectivity of conotoxins is at least in part defined by a specific disulfide bond frameworks combined with hypervariable amino acids within disulfide loops (for a review see McIntosh et al., 1998).

Due to the high potency and exquisite selectivity of the conopeptides, several are in various stages of clinical development for treatment of human disorders. For example, two *Conus* peptides are being developed for the treatment of pain. The most advanced is ω-conotoxin MVIIA (ziconotide), an N-type calcium channel blocker (see Heading, C., 1999; U.S. Pat. No. 5,859,186). ω-Conotoxin MVIIA, isolated from *Conus magus*, is approximately 1000 times more potent than morphine, yet does not produce the tolerance or addictive properties of opiates. ω-Conotoxin MVIIA has completed Phase III (final stages) of human clinical trials and has been approved as a therapeutic agent. ω-Conotoxin MVIIA is introduced into human patients by means of an implantable, programmable pump with a catheter threaded into the intrathecal space. Preclinical testing for use in post-surgical pain is being carried out on another *Conus* peptide, contulakin-G, isolated from *Conus geographus* (Craig et al. 1999). Contulakin-G is a 16 amino acid O-linked glycopeptide whose C-terminus resembles neurotensin. It is an agonist of neurotensin receptors, but appears significantly more potent than neurotensin in inhibiting pain in in vivo assays.

In view of a large number of biologically active substances in *Conus* species it is desirable to further characterize them and to identify peptides capable of treating disorders involving ion channels, ligand-gated channels, or receptors. Surprisingly, and in accordance with this invention, Applicants have discovered novel conopeptides that can be useful for the treatment of disorders involving ion channels, ligand-gated channels, or receptors and could address a long felt need for a safe and effective treatment.

SUMMARY OF THE INVENTION

The invention relates to novel conopeptides and/or novel uses of conopeptides as described herein. More specifically, the present invention is directed to the conopeptide α-conotoxin MII analogs ((α-MII) as described herein that are selective for α6-containing nicotinic acetylcholine receptors.

The present invention is further directed to derivatives of the conopeptides described herein or pharmaceutically acceptable salts of these peptides. Substitutions of one amino acid for another can be made at one or more additional sites within the described peptides, and may be made to modulate one or more of the properties of the peptides. Substitutions of this kind are preferably conservative, i.e., one amino acid is replaced with one of similar shape and charge. Conservative substitutions are well known in the art and include, for example: alanine to glycine, arginine to lysine, asparagine to glutamine or histidine, glycine to proline, leucine to valine or isoleucine, serine to threonine, phenylalanine to tyrosine, and the like.

These derivatives also include peptides in which the Pro residues may be substituted by hydroxy-Pro (Hyp); the Glu residues may be substituted by γ-carboxyglutamate (Gla); the Arg residues may be substituted by Lys, ornithine, homoargine, nor-Lys, N-methyl-Lys, N,N-dimethyl-Lys, N,N,N-trimethyl-Lys or any synthetic basic amino acid; the Lys residues may be substituted by Arg, ornithine, homoargine, nor-Lys, N-methyl-Lys, N,N-dimethyl-Lys, N,N,N-trimethyl-Lys or any synthetic basic amino acid; the Tyr residues may be substituted with meta-Tyr, ortho-Tyr, nor-Tyr, mono-halo-Tyr, di-halo-Tyr, O-sulpho-Tyr, O-phos-plho-Tyr, nitro-Tyr or any synthetic hydroxy containing amino acid; the Ser residues may be substituted with Thr or any synthetic hydroxylated amino acid; the Thr residues may be substituted with Ser or any synthetic hydroxylated amino acid; the Phe residues may be substituted with any synthetic aromatic amino acid; the Trp residues may be substituted with Trp (D), neo-Trp, halo-Trp (D or L) or any aromatic synthetic amino acid; and the Asn, Ser, Tlir or Hyp residues may be glycosylated. The halogen may be iodo, radioiodo, chloro, fluoro or bromo; preferably iodo for halogen substituted-Tyr and bromo for halogen-substituted Trp. The Tyr residues may also be substituted with the 3-hydroxyl or 2-hydroxyl isomers (meta-Tyr or ortho-Tyr, respectively) and corresponding O-sulpho- and O-phospho-derivatives. The acidic amino acid residues may be substituted with any synthetic acidic amino acid, e.g., tetrazolyl derivatives of Gly and Ala. The Met residues may be substituted with norleucine (Nle). The aliphatic amino acids may be substituted by synthetic derivatives bearing non-natural aliphatic branched or linear side chains $C_nH_{2n+2}$ up to and including n=8. The Leu residues may be substituted with Leu (D). The Gla residues may be substituted with Glu. The N-terminal Gln residues may be substituted with pyroGlu.

The present invention is further directed to derivatives of the above peptides and peptide derivatives which are acylic permutations in which the cyclic pennutants retain the native bridging pattern of native toxin. See Craik et al. (2001).

Examples of synthetic aromatic amino acid include, but are not limited to, nitro-Phe, 4-substituted-Phe wherein the substituent is $C_1$-$C_3$ alkyl, carboxyl, hyrdroxymiethyl, sulphomethyl, halo, phenyl, —CHO, —CN, —SO$_3$H and —NHAc. Examples of synthetic hydroxy containing amino acid, include, but are not limited to, such as 4-hydroxymnethyl-Phe, 4-hydroxyphenyl-Gly, 2,6-dimethyl-Tyr and 5-amino-Tyr. Examples of synthetic basic amino acids include, but are not limited to, N-1-(2-pyrazolinyl)-Arg, 2-(4-piperinyl)-Gly, 2-(4-piperinyl)-Ala, 2-[3-(2S)pyrrolininyl)-Gly and 2-[3-(2S)pyrrolininyl)-Ala. These and other synthetic basic amino acids, synthetic hydroxy containing amino acids or synthetic aromatic amino acids are described in Building Block Index, Version 3.0 (1999 Catalog, pages 4-47 for hydroxy containing amino acids and aromatic amino acids and pages 66-87 for basic amino acids; see also http://www.amino-acid-s.com), incorporated herein by reference, by and available from RSP Amino Acid Analogues, Inc., Worcester, Mass. Examples of synthetic acid amino acids include those derivatives bearing acidic functionality, including carboxyl, phosphate, sulfonate and synthetic tetrazolyl derivatives such as described by Ornstein et al. (1993) and in U.S. Pat. No. 5,331,001, each incorporated herein by reference, and such as shown in the following schemes 1-3.

Scheme 1

R = COOH, tetazole, CH$_2$COOH, 4-NHSO$_2$CH$_3$, 4-NHSO$_2$Phenyl, 4-CH$_2$SO$_3$H, SO$_3$H, 4-CH$_2$PO$_3$H$_2$, CH$_2$CH$_2$COOH, OCH$_2$Tetrazole, CH$_2$STetrazole, HNTetrazole, CONHSO$_2$R$_1$ where R$_1$ is CH$_3$ or Phenyl, SO$_2$-Tetrazole, CH$_2$CH$_2$SO$_3$H, 1,2,4-tetrazole, 3-isoxazolone, amidotetrazole, CH$_2$CH$_2$PO$_3$H$_2$ Scheme 2

R = COOH, tetrazole, CH$_2$COOH, CH$_2$tetrazole

Scheme 3

R = COOH, tetazole, CH$_2$COOH, 4-NHSO$_2$CH$_3$, 4-NHSO$_2$Phenyl, 4-CH$_2$SO$_3$H, SO$_3$H, 4-CH$_2$PO$_3$H$_2$, CH$_2$CH$_2$COOH, OCH$_2$Tetrazole, CH$_2$STetrazole, HNTetrazole, CONHSO$_2$R$_1$ where R$_1$ is CH$_3$ or Phenyl, SO$_2$-Tetrazole, CH$_2$CH$_2$SO$_3$H, 1,2,4-tetrazole, 3-isoxazolone, amidotetrazole, CH$_2$CH$_2$PO$_3$H$_2$; n = 0, 1, 2, or 3

Optionally, in the conopeptides of the present invention, the Asn residues may be modified to contain an N-glycan and the Ser, Thr and Hyp residues may be modified to contain an O-glycan (e.g., g-N, g-S, g-T and g-Hyp). In accordance with the present invention, a glycan shall mean any N-, S- or O-linked mono-, di-, tri-, poly- or oligosaccharide that can be attached to any hydroxy, amino or thiol group of natural or modified amino acids by synthetic or enzymatic methodologies known in the art. The monosaccharides making up the glycan can include D-allose, D-altrose, D-glucose, D-mannose, D-gulose, D-idose, D-galactose, D-talose, D-galactosamine, D-glucosamine, D-N-acetyl-glucosamine (GlcNAc), D-N-acetyl-galactosamine (GalNAc), D-fucose or D-arabinose. These saccharides may be structurally modified, e.g., with one or more O-sulfate, O-phosphate, O-acetyl or acidic groups, such as sialic acid, including combinations thereof. The gylcan may also include similar polyhydroxy groups, such as D-penicillamine 2,5 and halogenated derivatives thereof or polypropylene glycol derivatives. The glycosidic linkage is beta and 1-4 or 1-3, preferably 1-3. The linkage between the glycan and the amino acid may be alpha or beta, preferably alpha and is 1-.

Core O-glycans have been described by Van de Steen et al. (1998), incorporated herein by reference. Mucin type O-linked oligosaccharides are attached to Ser or Thr (or other hydroxylated residues of the present peptides) by a GalNAc residue. The monosaccharide building blocks and the linkage attached to this first GalNAc residue define the "core glycans," of which eight have been identified. The type of glycosidic linkage (orientation and connectivities) are defined for each core glycan. Suitable glycans and glycan analogs are described further in U.S. patent application Ser. No. 09/420,797 filed 19 Oct. 1999 now U.S. Pat. No. 6,369,193 and in International Patent Application No. PCT/US99/24380 filed 19 Oct. 1999 (publication No. WO 00/23092), each incorporated herein by reference. A preferred glycan is Gal(β1→3) GalNAc(α1→).

Optionally, in the peptides of general formula I and the specific peptides described above, pairs of Cys residues may be replaced pairwise with isoteric lactam or ester-thioether replacements, such as Ser/(Glu or Asp), Lys/(Glu or Asp), Cys/(Glu or Asp) or Cys/Ala combinations. Sequential coupling by known methods (Barnay et al., 2000; Hruby et al., 1994; Bitan et al., 1997) allows replacement of native Cys bridges with lactam bridges. Thioether analogs may be readily synthesized using halo-Ala residues commercially available from RSP Amino Acid Analgues. In addition, individual Cys residues may be replaced with homoCys, seleno-Cys or penicillamine, so that disulfide bridges may be formed between Cys-homoCys or Cys-penicillamine, or homocys-penicllamine and the like.

BRIEF DESCRIPTION OF THE FIGURES

FIG. 1A: α-Conotoxin MII blocked α3β2 and α6/α3β2β3 with $IC_{50}$ values of 2.18 and 0.39 nM, respectively. See also Table 1 for confidence intervals. The Hill slopes were 0.75±0.13 and 0.53±0.04, respectively. FIG. 1B: MII[H9A] blocked α3β2 and α6/α3β2β3 nAChRs with $IC_{50}$ values of 59.0 and 0.79 nM, respective, and with Hill slopes of 0.83±0.08 and 0.73±0.08. FIG. 1C: MII[L15A] blocked α3β2 and α6/α3β2β3 nAChRs with $IC_{50}$ values of 34 and 0.92 nM, respectively, and with Hill slopes of 0.58±0.08 and 0.75±0.08, respectively. The data are from three to six separate oocytes; ±value is the standard error of the mean.

FIGS. 2A and 2B show the concentration-response analysis of α-conotoxin MII[E11A] on nAChR subtypes expressed in $X.$ $laevis$ oocytes. Peptide was perfusion-applied at concentrations >100 nM and bath-applied at higher concentrations as described in the Examples. FIG. 2A: block by MII [E11A] of β02-containing nAChRs. FIG. 2B: block by MII [E11A] of β04-containing and α7 nAChRs. Data are from three to five oocytes. Error bars are S.E.M. Results are summarized in Table 2. Note the strong preference for α6/α3* nAChRs.

FIG. 3A: the peptide blocked rat α3β2 with an $IC_{50}$ of 4.8 μM (CI=3.5-6.6 μM) and $n_H$ of 0.48±0.04. The peptide blocked rat α6/α3β2β3 with an $IC_{50}$ of 2.4 nM (CI=1.7-3.4 nM) and $n_H$ of 0.72±0.09. FIG. 3B: the peptide blocked rat α3β4 with an $IC_{50}$ of 7.8 μM (CI=5.3-11.5 μM) and $n_H$ of 0.75±0.1. The peptide blocked rat α6β4 with an $IC_{50}$ of 269 nM (CI=153-476 nM) and $n_H$ of 0.60±0.09; ±values are standard error of the mean.

DETAILED DESCRIPTION OF THE PREFERRED EMBODIMENT

Figure 1A:
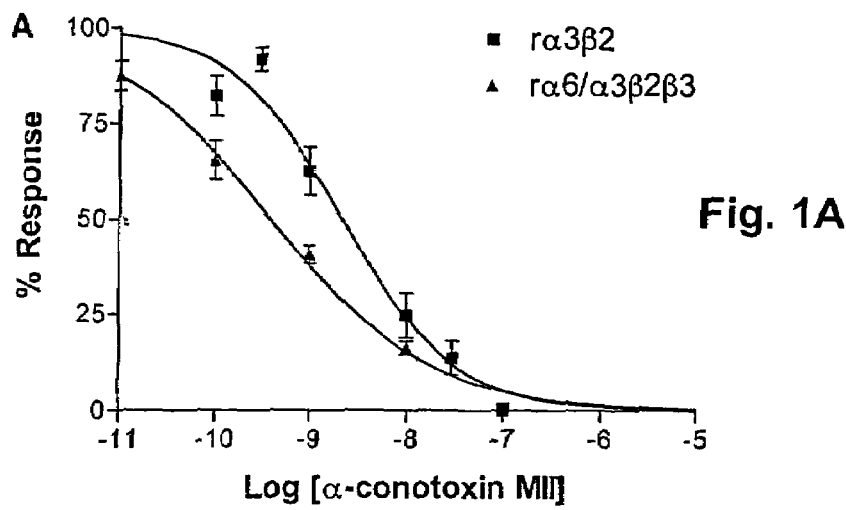
FIGS. 1A-1C show that H9A and L15A analogs of α-MII discriminate between α6/α3β2β3 and α3β2 nAChRs. Rat nAChR subunits were heterologously expressed in $X.$ $laevis$ oocytes. Concentration-response analysis of the peptide block of ACh-induced current was performed as described in the Examples.

The present invention is directed to novel conopeptides and/or novel uses of conopeptides as described herein. More specifically, the present invention is directed to the conopeptide α-conotoxin MII analogs (α-MII) as described herein that are selective for α6-containing nicotinic acetylcholine receptors.

The sequence for α-conotoxin MII and the (α-conotoxin MII analogs described herein are set forth in Table A.

TABLE A

Analogs of α-Conotoxin MII

| | Sequence (SEQ ID NO) | Calculated | Observed | Method |
|---|---|---|---|---|
| α-Conotoxin MII | GCCSNPVCHLEHSNLC* (1) | 1710.66 | 1711.0 | MALDI |
| Analog: S4A | GCCANPVCHLEHSNLC* (2) | 1694.67 | 1694.7 | LSIMS |
| N5A | GCCSAPVCHLEHSNLC* (3) | 1667.65 | 1667.6 | LSIMS |
| P6A | GCCSNAVCHLEHSNLC* (4) | 1684.64 | 1684.6 | LSIMS |
| V7A | GCCSNPACHLEHSNLC* (5) | 1682.63 | 1682.7 | MALDI |

TABLE A-continued

Analogs of α-Conotoxin MII

| | Sequence (SEQ ID NO) | | Calculated | Observed | Method |
|---|---|---|---|---|---|
| H9A | GCCSNPVCALEHSNLC* | (6) | 1644.64 | 1644.6 | MALDI |
| L10A | GCCSNPVCHAEHSNLC* | (7) | 1668.61 | 1668.6 | MALDI |
| E11A | GCCSNPVCHLAHSNLC* | (8) | 1652.65 | 1652.6 | MALDI |
| H12A | GCCSNPVCHLEASNLC* | (9) | 1644.64 | 1644.7 | MALDI |
| S13A | GCCSNPVCHLEHANLC* | (10) | 1694.67 | 1694.6 | LSIMS |
| N14A | GCCSNPVCHLEHSALC* | (11) | 1667.65 | 1667.6 | LSIMS |
| L15A | GCCSNPVCHLEHSNAC* | (12) | 1668.61 | 1668.6 | MALDI |
| H9A; L15A | GCCSNPVCALEHSNAC* | (13) | 1602.59 | 1602.6 | MALDI |
| L10A; L15A | GCCSNPVCHAEHSNAC* | (14) | 1626.57 | 1626.6 | MALDI |
| E11A; L15A | GCCSNPVCHLAHSNAC* | (15) | 1610.61 | 1610.6 | MALDI |
| S4A; H9A | GCCANPVCALEHSNLC* | (16) | 1628.64 | 1628.69 | MALDI |

MALDI, matrix-assisted laser desorption ionization time-of-flight mass spectrometry;
LSIMS, liquid secondary ionization mass spectrometry;
*amidated C-terminus.

Neuronal nicotinic acetylcholine receptors (nAChRs) activated by the endogenous neurotransmitter acetylcholine belong to the superfamily of ligand-gated ion channels that also includes $GABA_A$, 5-hydroxytryptamine-3, and glycine receptors (Changeux, 1993). These different ligand-gated ion channels show considerable sequence and structural homology. Each of the subunits has a relatively hydrophilic amino terminal half (~200 amino acids) that constitutes an extracellular domain. This is followed by three hydrophobic transmembrane domains, a large intracellular loop, and then a fourth hydrophobic transmembrane span.

A large number of genes have been cloned that encode subunits of nAChRs. It has been proposed that these subunits may be divided into subfamilies on the basis of both gene structure and mature protein sequence. The subunits α2, α3, α4, and α6 belong to subfamily III, tribe 1; β2 and β4 belong to tribe III -2; and the putative structural subunits α5 and β3 belong to tribe III-3 (Corringer et al., 2000). Within tribe III-1, subunits α3 and α6 show considerable sequence identity (~80% in the ligand-binding extracellular domain). Thus, designing ligands to distinguish between α3* and α6* is particularly challenging.

α-Conotoxin MII is a 16 amino acid peptide originally isolated from the venom of the marine snail Conus magus. This peptide potently targets neuronal in preference to the muscle subtype of nicotinic receptor with high affinity for both α3β2 and α6* nAChRs. Unfortunately, α-conotoxin MII may not distinguish well between α3* and α6* nAChRs (Kuryatov et al., 2000). In an effort to remedy this situation and produce a selective ligand for α6* nAChRs, a series of α-conotoxin MII analogs have been generated as described herein.

The α6 subunit is expressed in catecholaminergic neurons and in retina (Le Novere et al., 1996, 1999; Vailati et al., 1999). In striatum, α6* nAChRs seem to play a central role in the modulation of dopamine release. Recently, homozygous null mutant (α6–/–) mice were generated. Receptor autoradiography studies in these animals indicate that the α6 nAChR subunit is a critical component of [$^{125}$I]α-conotoxin MII binding in the central nervous system (Champtiaux et al., 2002). Studies using mice with nAChR subunit deletion indicate that α3 does not participate in most [$^{125}$I]α-conotoxin MII binding sites but does influence expression in the habenulo-peduncular tract (Whiteaker et al., 2002). Thus, α6-selective ligands is useful to distinguish the α6* majority form from the α3* minority of such sites.

More specifically, Neuronal nicotinic acetylcholine receptors (nAChRs) both mediate direct cholinergic synaptic transmission and modulate synaptic transmission by other neurotransmitters. Novel ligands are needed as probes to discriminate among structurally related nAChR subtypes. α-Conotoxin MII, a selective ligand that discriminates among a variety of nAChR subtypes, fails to discriminate well between some subtypes containing the closely related α3 and α6 subunits. Structure-function analysis of α-conotoxin MII was performed in an attempt to generate analogs with preference for α6-containing [α6* (asterisks indicate the possible presence of additional subunits)] nAChRs. Alanine substitution resulted in several analogs with decreased activity at α3* versus α6* nAChRs heterologously expressed in Xenopus laevis oocytes.

From the initial analogs, a series of mutations with two alanine substitutions was synthesized. Substitution at His9 and Leu15 (MII[H9A;L15A]) resulted in a 29-fold lower $IC_{50}$ at α6β4 versus α3β4 nAChRs. The peptide had a 590-fold lower $IC_{50}$ for α6/α3β2 versus α3β2 and a 2020-fold lower $IC_{50}$ for α6/α3β2β3 versus α3β2 nAChRs. MII[H9A;L15A] had little or no activity at α2β2, α2β4, α3β4, α4β2, α4β4, and α7 nAChRs. Functional block by MII[H9A;L15A] of rat α6/α3β2β3 nAChRs ($IC_{50}$=2.4 nM) correlated well with the inhibition constant of MII[H9A;L15A] for [$^{125}$I]α-conotoxin MII binding to putative α6β2* nAChRs in mouse brain homogenates ($K_i$=3.3 nM). Thus, structure-function analysis of α-conotoxin MII enabled the creation of novel selective antagonists for discriminating among nAChRs containing α3 and α6 subunits.

Although the conopeptides of the present invention can be obtained by purification from cone snails, because the amounts of peptide obtainable from individual snails are very small, the desired substantially pure peptides are best practically obtained in commercially valuable amount by chemical synthesis using solid-phase strategy. For example, the yield from a single cone snail may be about 10 micrograms or less of peptide. By "substantially pure" is meant that the peptide is present in the substantial absence of other biological molecules of the same type; it is preferably present in an amount of at least about 85% purity and preferably at least about 95% purity.

The peptides of the present invention can also be produced by recombinant DNA techniques well known in the art. Such techniques are described by Sambrook et al. (1989). A gene of interest can be inserted into a cloning site of a suitable expression vector by using standard techniques. These techniques are well known to those skilled in the art. The expression vector containing the gene of interest may then be used to transfect the desired cell line. Standard transfection techniques such as calcium phosphate co-precipitation, DEAE-dextran transfection or electroporation may be utilized. A wide variety of host/expression vector combinations may be used to express a gene encoding a conotoxin peptide of interest. Such combinations are well known to a skilled artisan. The peptides produced in this manner are isolated, reduced if necessary, and oxidized, if necessary, to form the correct disulfide bonds.

One method of forming disulfide bonds in the peptides of the present invention is the air oxidation of the linear peptides for prolonged periods under cold room temperatures or at room temperature. This procedure results in the creation of a substantial amount of the bioactive, disulfide-linked peptides. The oxidized peptides are fractionated using reverse-phase high performance liquid chromatography (HPLC) or the like, to separate peptides having different linked configurations. Thereafter, either by comparing these fractions with the elution of the native material or by using a simple assay, the particular fraction having the correct linkage for maximum biological potency is easily determined. However, because of the dilution resulting from the presence of other fractions of less biopotency, a somewhat higher dosage may be required.

The peptides are synthesized by a suitable method, such as by exclusively solid-phase techniques, by partial solid-phase techniques, by fragment condensation or by classical solution couplings.

In conventional solution phase peptide synthesis, the peptide chain can be prepared by a series of coupling reactions in which constituent amino acids are added to the growing peptide chain in the desired sequence. Use of various coupling reagents, e.g., dicyclohexylcarbodiimide or diisopropylcarbonyldimidazole, various active esters, e.g., esters of N-hydroxyphthalimide or N-hydroxy-succinimide, and the various cleavage reagents, to carry out reaction in solution, with subsequent isolation and purification of intermediates, is well known classical peptide methodology. Classical solution synthesis is described in detail in the treatise, "Methoden der Organischen Chemie (Houben-Weyl): Synthese von Peptiden," (1974). Techniques of exclusively solid-phase synthesis are set forth in the textbook, "Solid-Phase Peptide Synthesis," (Stewart and Young, 1969), and are exemplified by the disclosure of U.S. Pat. No. 4,105,603 (Vale et al., 1978). The fragment condensation method of synthesis is exemplified in U.S. Pat. No. 3,972,859 (1976). Other available syntheses are exemplified by U.S. Pat. No. 3,842,067 (1974) and 3,862,925 (1975). The synthesis of peptides containing -carboxy-glutamic acid residues is exemplified by Rivier et al. (1987), Nishiuchi et al. (1993) and Zhou et al. (1996).

Common to such chemical syntheses is the protection of the labile side chain groups of the various amino acid moieties with suitable protecting groups that will prevent a chemical reaction from occurring at that site until the group is ultimately removed. Usually also common is the protection of an α-amino group on an amino acid or a fragment while that entity reacts at the carboxyl group, followed by the selective removal of the α-amino protecting group to allow subsequent reaction to take place at that location. Accordingly, it is common that, as a step in such a synthesis, an intermediate compound is produced which includes each of the amino acid residues located in its desired sequence in the peptide chain with appropriate side-chain protecting groups linked to various ones of the residues having labile side chains.

As far as the selection of a side chain amino protecting group is concerned, generally one is chosen which is not removed during deprotection of the α-amino groups during the synthesis. However, for some amino acids, e.g., His, protection is not generally necessary. In selecting a particular side chain protecting group to be used in the synthesis of the peptides, the following general rules are followed: (a) the protecting group preferably retains its protecting properties and is not split off under coupling conditions, (b) the protecting group should be stable under the reaction conditions selected for removing the α-amino protecting group at each step of the synthesis, and (c) the side chain protecting group must be removable, upon the completion of the synthesis containing the desired amino acid sequence, under reaction conditions that will not undesirably alter the peptide chain.

It should be possible to prepare many, or even all, of these peptides using recombinant DNA technology. However, when peptides are not so prepared, they are preferably prepared using the Merrifield solid-phase synthesis, although other equivalent chemical syntheses known in the art can also be used as previously mentioned. Solid-phase synthesis is commenced from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or paramethylbenzhydrylamine (MBHA) resin. Preparation of the hydroxymethyl resin is described by Bodansky et al. (1966). Chloromethylated resins are commercially available from Bio Rad Laboratories (Richmond, Calif.) and from Lab. Systems, Inc. The preparation of such a resin is described by Stewart and Young (1969). BHA and MBHA resin supports are commercially available, and are generally used when the desired polypeptide being synthesized has an unsubstituted amide at the C-terminus. Thus, solid resin supports may be any of those known in the art, such as one having the formulae —O—CH$_2$-resin support, —NH BHA resin support, or —NH-MBHA resin support. When the unsubstituted amide is desired, use of a BHA or MBHA resin is preferred, because cleavage directly gives the amide. In case the N-methyl amide is desired, it can be generated from an N-methyl BHA resin. Should other substituted amides be desired, the teaching of U.S. Pat. No. 4,569,967 (Kornreich et al., 1986) can be used, or should still other groups than the free acid be desired at the C-terminus, it may be preferable to synthesize the peptide using classical methods as set forth in the Houben-Weyl text (1974).

The C-terminal amino acid, protected by Boc or Fmoc and by a side-chain protecting group, if appropriate, can be first coupled to a chloromethylated resin according to the procedure set forth in Horiki et al. (1978), using KF in DMF at about 60° C. for 24 hours with stirring, when a peptide having free acid at the C-terminus is to be synthesized. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups may be used as described in Schroder & Lubke (1965).

After removal of the (α-amino-protecting group, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. Selection of an appropriate coupling reagent is within the skill of the art. Particularly suitable as a coupling reagent is N,N'-dicyclohexylcarbodiimide (DCC, DIC, HBTU, HATU, TBTU in the presence of HoBt or HoAt).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)acarbodiimide. Other activating reagents and their use in peptide coupling are described by Schroder & Lubke (1965) and Kapoor (1970).

Each protected amino acid or amino acid sequence is introduced into the solid-phase reactor in about a twofold or more excess, and the coupling may be carried out in a medium of dimethylformamide (DMF):$CH_2Cl_2$ (1:1) or in DMF or $CH_2Cl_2$ alone. In cases where intermediate coupling occurs, the coupling procedure is repeated before removal of the (α-amino protecting group prior to the coupling of the next amino acid. The success of the coupling reaction at each stage of the synthesis, if performed manually, is preferably monitored by the ninhydrin reaction, as described by Kaiser et al. (1970). Coupling reactions can be performed automatically, as on a Beckman 990 automatic synthesizer, using a program such as that reported in Rivier et al. (1978).

After the desired amino acid sequence has been completed, the intermediate peptide can be removed from the resin support by treatment with a reagent, such as liquid hydrogen fluoride or TFA (if using Fmoc chemistry), which not only cleaves the peptide from the resin but also cleaves all remaining side chain protecting groups and also the α-amino protecting group at the N-terminus if it was not previously removed to obtain the peptide in the form of the free acid. If Met is present in the sequence, the Boc protecting group is preferably first removed using trifluoroacetic acid (TFA)/ethanedithiol prior to cleaving the peptide from the resin with HF to eliminate potential S-alkylation. When using hydrogen fluoride or TFA for cleaving, one or more scavengers such as anisole, cresol, dimethyl sulfide and methylethyl sulfide are included in the reaction vessel.

Cyclization of the linear peptide is preferably affected, as opposed to cyclizincg the peptide while a part of the peptido-resin, to create bonds between Cys residues. To effect such a disulfide cyclizing linkage, fully protected peptide can be cleaved from a hydroxymetlhylated resin or a chloromethylated resin support by ammonolysis, as is well known in the art, to yield the fully protected amide intermediate, which is thereafter suitably cyclized and deprotected. Alternatively, deprotection, as well as cleavage of the peptide from the above resins or a benzhydrylamine (BHA) resin or a methyl-benzlhydrylamine (MBHA), can take place at 0° C. with hydrofluoric acid (HF) or TFA, followed by oxidation as described above.

The peptides are also synthesized using an automatic synthesizer. Amino acids are sequentially coupled to an MBHA Rink resin (typically 100 mg of resin) beginning at the C-terminus using an Advanced Chemtech 357 Automatic Peptide Synthesizer. Couplings are carried out using 1,3-diisopropylcarbodiimide in N-methylpyrrolidinone (NMP) or by 2-(1H-benzotriazole-1-yl)-1,1,3,3-tetramethyluronium hexafluoroplhosphate (HBTU) and diethylisopro-pylethylamine (DIEA). The FMOC protecting group is removed by treatment with a 20% solution of piperidine in dimethylfonnamide (DMF). Resins are subsequently washed with DMF (twice), followed by methanol and NMP.

The incorporation of the radiometal into a conopeptide can be accomplished at a Tyr residue for radio-iodine or will generally involve the use of a chelate, specific to the particular metal, and a linker group to covalently attach the chelate to the conotoxin, i.e., a the bifunctional chelate approach. The design of useful chelates is dependent on the coordination requirements of the specific radiometal. DTPA, DOTA, $P_2S_2$—COOH BFCA requirement for kinetic TETA, NOTA are common examples. The requirement for kinetic stability of the metal complex is often achieved through the use of multidentate chelate ligands with a functionalized arm for covalent bonding to some part of the conantokin or γ-carboxyglutamate containing conopeptide, i.e., the lysine amino group. Techniques for chelating radioonuclides with proteins are well known in the art, such as demonstrated by interantional patent application publication No. WO 91/01144, incorporated herein by reference.

Pharmaceutical compositions containing a compound of the present invention as the active ingredient can be prepared according to conventional pharmaceutical compounding techniques. See, for example, *Remingtoin's Pharmaceutical Scienices,* 18th Ed. (1990, Mack Publishing Co., Easton, Pa.). Typically, an antagonistic amount of active ingredient will be admixed with a pharmaceutically acceptable carrier. The carrier may take a wide variety of forms depending on the form of preparation desired for administration, e.g., intravenous, oral, parenteral or intrathecally. For examples of delivery methods see U.S. Pat. No. 5,844,077, incorporated herein by reference.

"Pharmaceutical composition" means physically discrete coherent portions suitable for medical administration. "Pharmaceutical composition in dosage unit form" means physically discrete coherent units suitable for medical administration, each containing a daily dose or a multiple (up to four times) or a sub-multiple (down to a fortieth) of a daily dose of the active compound in association with a carrier and/or enclosed within an envelope. Whether the composition contains a daily dose, or for example, a half, a third or a quarter of a daily dose, will depend on whether the pharmaceutical composition is to be administered once or, for example, twice, three times or four times a day, respectively.

The term "salt", as used herein, denotes acidic and/or basic salts, formed with inorganic or organic acids and/or bases, preferably basic salts. While pharmaceutically acceptable salts are preferred, particularly when employing the compounds of the invention as medicaments, other salts find utility, for example, in processing these compounds, or where non-medicament-type uses are contemplated. Salts of these compounds may be prepared by art-recognized techniques.

Examples of such pharmaceutically acceptable salts include, but are not limited to, inorganic and organic addition salts, such as hydrochloride, sulphates, nitrates or phosphates and acetates, trifluoroacetates, propionates, succinates, benzoates, citrates, tartrates, fumarates, maleates, methane-sulfonates, isothionates, theophylline acetates, salicylates, respectively, or the like. Lower alkyl quaternary ammonium salts and the like are suitable, as well.

As used herein, the tern "pharmaceutically acceptable" carrier means a non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations.

Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Examples of pharmaceutically acceptable antioxidants include, but are not limited to, water soluble antioxidants such as ascorbic acid, cysteine hydrochloride, sodium bisulfite, sodium metabisulfite, sodium sulfite, and the like; oil soluble antioxidants, such as ascorbyl palmitate, butylated hydroxyaniisole (BHA), butylated hydroxytoluene (BHT), lecithin, propyl gallate, aloha-tocopherol and the like; and the metal chelating agents such as citric acid, ethylenediamine tetraacetic acid (EDTA), sorbitol, tartaric acid, phosphoric acid and the like.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, ill which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

A variety of administration routes are available. The particular mode selected will depend of course, upon the particular drug selected, the severity of the disease state being treated and the dosage required for therapeutic efficacy. The methods of this invention, generally speaking, may be practiced using any mode of administration that is medically acceptable, meaning any mode that produces effective levels of the active compounds without causing clinically unacceptable adverse effects. Such modes of administration include oral, rectal, sublingual, topical, nasal, transdermal or parenteral routes. The term "parenteral" includes subcutaneous, intravenous, epidural, irrigation, intramuscular, release pumps, or infusion.

For example, administration of the active agent according to this invention may be achieved using any suitable delivery means, including:

(a) pump (see, e.g., Luer & Hatton (1993), Zimm et al. (1984) and Ettinger et al. (1978));

(b), microencapsulation (see, e.g., U.S. Pat. Nos. 4,352,883; 4,353,888; and 5,084,350);

(c) continuous release polymer implants (see, e.g., U.S. Pat. No. 4,883,666);

(d) macroencapsulation (see, e.g., U.S. Pat. Nos. 5,284,761; 5,158,881, 4,976,859 and 4,968,733 and published PCT patent applications WO92/19195, WO 95/05452);

(e) naked or unencapsulated cell grafts to the CNS (see, e.g., U.S. Pat. Nos. 5,082,670 and 5,618,531);

(f) injection, either subcutaneously, intravenously, intra-arterially, intramuscularly, or to other suitable site; or (g) oral administration, in capsule, liquid, tablet, pill, or prolonged release formulation.

In one embodiment of this invention, an active agent is delivered directly into the CNS, preferably to the brain ventricles, brain parenchyma, the intrathecal space or other suitable CNS location, most preferably intrathecally.

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

The active agents, which are peptides, can also be administered in a cell based delivery system in which a DNA sequence encoding an active agent is introduced into cells designed for implantation in the body of the patient, especially in the spinal cord region. Suitable delivery systems are described in U.S. Pat. No. 5,550,050 and published PCT Application Nos. WO 92/19195, WO 94/25503, WO 95/01203, WO 95/05452, WO 96/02286, WO 96/02646, WO 96/40871, WO 96/40959 and WO 97/12635. Suitable DNA sequences can be prepared synthetically for each active agent on the basis of the known peptide sequences and disclosed DNA sequences.

The active agent is preferably administered in an therapeutically effective amount. By a "therapeutically effective amount" or simply "effective amount" of an active compound is meant a sufficient amount of the compound to treat the desired condition at a reasonable benefit/risk ratio applicable to any medical treatment. The actual amount administered, and the rate and time-course of administration, will depend on the nature and severity of the condition being treated. Prescription of treatment, e.g. decisions on dosage, timing, etc., is within the responsibility of general practitioners or spealists, and typically takes account of the disorder to be treated, the condition of the individual patient, the site of delivery, the method of administration and other factors known to practitioners. Examples of techniques and protocols can be found in *Remington's Parmaceutical Sciences*.

Dosage may be adjusted appropriately to achieve desired levels, locally or systemically, and depending on use as a diagnostic agent or a therapeutic agent. Typically the conopeptides of the present invention exhibit their effect at a dosage range from about 0.001 mg/kg to about 250 mg/kg, preferably from about 0.05 mg/kg to about 100 mg/kg of the active ingredient, more preferably from a bout 0.1 mg/kg to about 75 mg/kg, and most preferably from about 1.0 mg/kg to about 50 mg/kg. A suitable dose can be administered in multiple sub-doses per day. Typically, a dose or sub-dose may contain from about 0.1 mg to about 500 mg of the active ingredient per unit dosage form. A more preferred dosage will contain from about 0.5 mg to about 100 mg of active ingredient per unit dosage form. Dosages are generally initiated at lower levels and increased until desired effects are achieved. In the event that the response in a subject is insufficient at such doses, even higher doses (or effective higher doses by a different, more localized delivery route) may be employed to the extent that patient tolerance permits. Continuous dosing over, for example 24 hours or multiple doses per day are contemplated to achieve appropriate systemic levels of compounds.

Advantageously, the compositions are formulated as dosage units, each unit being adapted to supply a fixed dose of active ingredients. Tablets, coated tablets, capsules, ampoules and suppositories are examples of dosage forms according to the invention.

It is only necessary that the active ingredient constitute an effective amount, i.e., such that a suitable effective dosage will be consistent with the dosage form employed in single or multiple unit doses. The exact individual dosages, as well as daily dosages, are determined according to standard medical principles under the direction of a physician or veterinarian for use humans or animals.

The pharmaceutical compositions will generally contain from about 0.0001 to 99 wt. %, preferably about 0.001 to 50 wt. %, more preferably about 0.01 to 10 wt.% of the active ingredient by weight of the total composition. In addition to the active agent, the pharmaceutical compositions and medicaments can also contain other pharmaceutically active compounds. Examples of other pharmaceutically active compounds include, but are not limited to, analgesic agents, cytokines and therapeutic agents in all of the major areas of clinical medicine. When used with other pharmaceutically active compounds, the conopeptides of the present invention may be delivered in the form of drug cocktails. A cocktail is a mixture of any one of the compounds useful with this invention with another drug or agent. In this embodiment, a common administration vehicle (e.g., pill, tablet, implant, pump, injectable solution, etc.) would contain both the instant composition in combination supplementary potentiating agent. The individual drugs of the cocktail are each administered in therapeutically effective amounts. A therapeutically effective amount will be determined by the parameters described above; but, in any event, is that amount which establishes a level of the drugs in the area of body where the drugs are required for a period of time which is effective in attaining the desired effects.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982; Sambrook et al., 1989; Ausubel et al., 1992; Glover, 1985; Anand, 1992; Guthrie and Fink, 1991; Harlow and Lane, 1988; Jakoby and Pastan, 1979; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Imnmunology*, Volumes I-IV (D. M. Weir and C. C. Blackwell, eds., 1986); Riott, *Essential Immunology*, 6th Edition, Blackwell Scientific Publications, Oxford, 1988; Hogan et al., Manipulating the Mouse Embryo, (Cold Spring Harbor Laboratory Press, Cold Spring Harbor, N.Y., 1986).

EXAMPLES

The present invention is described by reference to the following, which are offered by way of illustration and are not intended to limit the invention in any manner. Standard techniques well known in the art or the techniques specifically described below were utilized.

Example 1

Materials and Methods

Chemical synthesis: Peptides were synthesized on a Rink amide resin, 0.45 mmol/g [Fmoc-Cys(Trityl)-Wang; Novabiochem, San Diego, Calif.] usinig N-(9-fluorenyl)methoxycarboxyl chemistry and standard side chain protection except on cysteine residues. Cysteine residues were protected in pairs with either S-trityl on the first and third cysteines or S-acetamidomethyl on the second and fourth cysteines. Amino acid derivatives were from Advanced Chemtech (Louisville, Ky.). The peptides were removed from the resin and precipitated, and a two-step oxidation protocol was used to selectively fold the peptides as described previously (Luo et al., 1999). Briefly, the first disulfide bridge was closed by dripping the peptide into an equal volume of 20 mM potassium ferricyanide and 0.1 M Tris, pH 7.5. The solution was allowed to react for 30 min, and the monocyclic peptide was purified by reverse-phase HPLC. Simultaneous removal of the S-acetamidomethyl groups and closure of the second disulfide bridge was carried out by iodine oxidation. The monocyclic peptide and HPLC eluent was dripped into an equal volume of iodine (10 mM) in $H_2O$/trifluoroacetic acid/acetonitrile (78:2:20 by volume) and allowed to react for 10 min. The reaction was terminated by the addition of ascorbic acid diluted 20-fold with 0.1% trifluoroacetic acid and the bicyclic product purified by HPLC.

Mass Spectrometry: Measurements were performed at the Salk Institute for Biological Studies (San Diego, Calif.) under the direction of Jean Rivier. Matrix-assisted laser desorption ionization time-of-flight mass spectrometry and liquid secondary ionization mass spectrometry were used.

Preparation of nAChR subunit cRNA: Attempts to express the rat nAChR α6 subtype in *Xenopus laevis* oocytes consistently failed; that is, no ACh-gated currents were detected. To improve functional expression, we created a chimeric receptor of the rat α6 and α3 subtypes. The chimeric receptor consists of amino acids 1 to 237 of the rat α6 subunit protein linked to amino acids 233 to 499 of the rat α3 subunit protein. The chimeric junction is located at the paired-RR-residues immediately preceding the M1 transmembrane segment of the α3 subunit. The resulting chimeric receptor represents the extracellular ligand-binding domain of the α6 subunit linked to membrane-spanning and intracellular segments of the α3 subunit. The α6/α3 cDNA was constructed by the introduction of BspEI sites at the chimeric junction into the α6 and α3 cDNA sequences using mutagenic primers to introduce the restriction sites through silent codon changes. The α6 and α3 segments were generated by polymerase chain reaction of rat brain cDNA using primers in the 5' and 3' untranslated regions of the corresponding cDNAs along with the internal mutagenic primers. The polymerase chain reaction products were digested with BspEI and ligated to generate the chimeric construct. The final chimeric construct was cloned and completely sequenced to confirm the correct cDNA sequence. To further improve expression levels, all of the 5' and 3' untranslated regions of the nAChR cDNA were deleted, and the chimeric construct was cloned into the X. laevis expression vector pT7TS, placing X laevis globin 5' and 3' untranslated regions around the nAChR cDNA. The expression construct pT7TS/rα6α3 was transcribed with T7 RNA polymerase to generate sense-strand RNA for oocyte expression.

Electrophysiology and data analysis: Clones of rat nAChR subunits were used to produce cRNA for injection into X laevis oocytes as described previously (Cartier et al., 1996). The rat α6 and β3 subunits were a generous gift from S. Heinemann (Salk Institute, San Diego, Calif.) (Deneris et al., 1989). To express nAChRs in oocytes, 5 ng of each nAClR subunit was injected. In the case of α6β4, 50 ng of each subunit was injected because of absent expression when using 5 ng of cRNA. Likewise, 20 ng was used for the α6/α3β2 combination that expresses poorly without the β3 subunit. A 30-μl cylindrical oocyte recording chamber fabricated from Sylgard was gravity-perfused with ND96A (96.0 mM NaCl, 2.0 mM KCl, 1.8 mM CaCl$_2$, 1.0 mM MgCl$_2$, 1 μM atropine, and 5 mM HEPES, pH 7.1-7.5) at a rate of ~2 ml/min (Luo et al., 1998). All toxin solutions also contained 0.1 mg/ml bovine serum albumin to reduce nonspecific adsorption of peptide. Toxin was preapplied for 5 min. ACh-gated currents were obtained with a 2-electrode voltage-clamp amplifier (model OC-725B; Warner Instrument, Hamden, Conn.), and data were captured as described previously (Luo et al., 1998). The membrane potential of the oocytes was clamped at −70 mV. To apply a pulse of ACh to the oocytes, the perfusion fluid was switched to one containing ACh for 1 s. This was done automatically at intervals of 1 to 5 min. The shortest time interval was chosen such that reproducible control responses were obtained with no observable desensitization. The concentration of ACh was 10 μM for trials with α1β1δεand 100 μM for all other nAChRs. Toxin was bath-applied for 5 min, followed by a pulse of ACh. Thereafter, toxin was washed away, and subsequent ACh pulses were given every 1 min, unless otherwise indicated. All ACh pulses contain no toxin, for it was assumed that little if any bound toxin washed away in the brief time (less than the 2 s it takes for the responses to peak). In our recording chamber, the bolus of ACh does not project directly at the oocyte but rather enters tangentially, swirls, and mixes with the bath solution. The volume of entering ACh is such that the toxin concentration remains at a level >$^{50}$% of that originally in the bath until the ACh response has peaked (<2 s). When longer than 5 min of toxin application was needed to reach maximum block, toxin was applied by continuous perfusion to the oocytes as described previously (Luo et al., 1994), except that ACh was applied once every 2 min.

The average peak amplitude of three control responses just preceding exposure to toxin was used to normalize the amplitude of each test response to obtain a "% response" or "% block". Each data point of a dose-response curve represents the average value± S.E. of measurements from at least three oocytes. Dose-response curves were fit to the equation % response=$100/\{1+([\text{toxin}]/\text{IC}_{50})^{n_H}\}$, where $n_H$ is the Hill slope determined with Prism software (Graph-Pad Software, San Diego, Calif.) on an Macintosh (Apple Computers, Cupertino, Calif.). For three or fewer data points, nH was set to 1.0.

Membrane preparation: Mice were killed by cervical dislocation. Brains were removed from the skulls and dissected on an ice-cold platform. Membranes containing [$^{125}$I]α-conotoxin MII binding sites were prepared from pooled olfactory tubercles, striatum, and superior colliculus. Samples were homogenized in 2× physiological buffer (288 mM NaCl; 3 mM KCl; 4 mM CaCl$_2$; 2 mM MgSO$_4$; and 40 mM HEPES, pH 7.5; 22° C.) using a glass-polytetrafluoroethyle tissue grinder. Homogenates were then treated with phenylmethylsulfonyl fluoride (final concentration, 1 mM; 15 min at 22° C.) to inactivate endogenous serine proteases before centrifugation (20,000 g for 20 min at 4° C.). Pellets were washed twice by homogenization in distilled deionized water glass-polytetrafluoroethylene tissue grinder, 4° C.) and centrifugation (20,000g for 20 min at 4° C.). Pooled tissue from a single mouse provided sufficient material for a single 96-well format assay.

Inhibition of [$^{125}$I] α-conotoxin MII binding: Inhibition of [$^{125}$I] α-conotoxin MII binding to mouse brain membranes was performed using a modified version of the 96-well plate procedure described previously (Whiteaker et al., 2000a). Assays were performed in triplicate using 1.2-ml siliconized polypropylene tubes arranged in a 96-well format. Membrane pellets were resuspended into distilled deionized water. Total (no drug) and nonspecific (with 1 μM epibatidine) binding determinations were included in each experiment for each drug dilution series. Initial incubations proceeded for 3 h at 22° C. in 1× protease inhibitor buffer [1× physiological buffer supplemented with bovine serum albumin (0.1% w/v), 5 mM EDTA, 5 mM EGTA, and 10 μg/ml each of aprotinin, leupeptin trifluoroacetate, and pepstatin A]. Each tube contained 10 μl of membrane preparation, 10 μl of competing ligand (or nonspecific or total determinations) in 1× protease inhibitor buffer, and 10 μl of [$^{125}$I]α-conotoxin MII (1.5 nM in 2× protease inhibitor buffer, giving a final assay radioligand concentration of 0.5 nM). After incubation, each tube was diluted with 1 ml of physiological buffer plus 0.1% (w/v) bovine serum albumin. Tubes were then incubated for a further 4 mil at 22° C. to reduce nonspecific binding to the membrane preparation. The binding reactions were then terminated by filtration onto a single thickness of GF/F filter paper (Whatman, Clifton, N.J.) using a cell harvester (Inotech Biosystems, Rockville, Md.). The filters were incubated previously for 15 min with 5% dried skim milk to reduce nonspecific binding. Assays were washed with four changes of physiological buffer supplemented with bovine serum albumin (0.1% w/v). Washes were performed at 30-s intervals, with each lasting approximately 5 s. All filtration and collection steps were performed at 4° C. Bound ligand was quantified for each filter disc by gamma counting using a Cobra II counter (≈85% efficiency) (PerkinElmer Life and Analytical Sciences, Boston, Mass.).

Calculations: Data from individual [$^{125}$I]α-conotoxin MII inhibition binding experiments were processed using a single-site fit using the nonlinear least-squares fitting algorithm of GraphPad Prism. Values of $K_i$ were derived for each experiment by the method described by Cheng and Prusoff (1973), $K_i=IC_{50}/1+(L/K_D)$, where $K_i$ for [$^{125}$I] α-conotoxin is 0.32 nM.

Example 2

Results

Peptide Synthesis: The sequence of native a-conotoxin MII is GCCSNPVCHLEHSNLC (SEQ ID NO: 1). Peptide analogs were synthesized by substituting one or more residues with alanine. These peptides are named according to the residue(s) substituted; for example, MII[E11A] has the glutamic acid in position 11 substituted with alanine. Cysteine residues were orthogonally protected to direct the formation of disulfide bonds in the configuration found in α-conotoxin MII, that is cysteine 1 to cysteine 3 and cysteine 2 to cysteine4. The first and third cysteine residues were protected with acid-labile groups that were removed first after a cleavage from the resin; ferricyanide was used to close the first disulfidebridge. The monocyclic peptides were purified by reverse-phase HPLC. Then the acid-stable acetamidomethyl groups were removed from the second and fourth cysteines by iodine oxidation that also closed the second disulfide bridge. The fully folded peptides were again purified by HPLC. Mass spectrometry was used to confirm synthesis. The observed molecular mass for each peptide was within 0.1 Da of the expected mass.

Figure 1B:
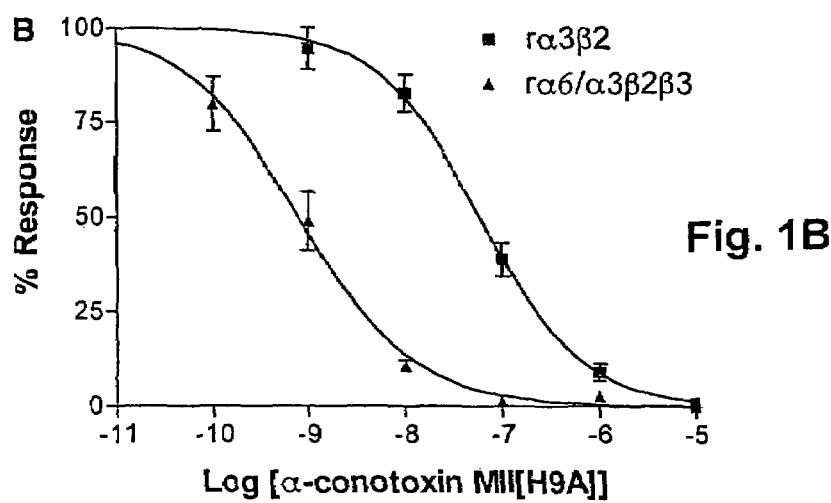
Figure 1C:
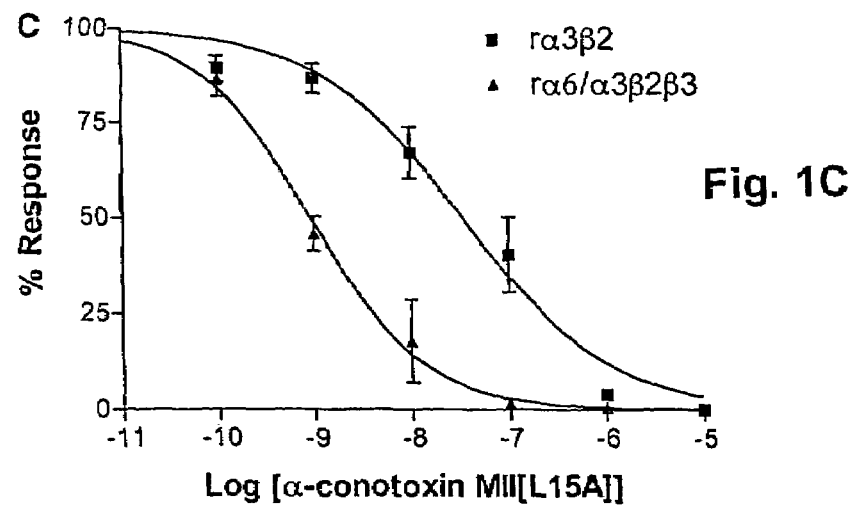

Peptide Effects on α6 and α3 nAChRs: Injection of rat α6 subunits into oocytes either alone or in combination with β2 and/or β3 subunits yields few or no functional nAChRs. Using a previously reported strategy for human α6 (Kuryatov et al., 2000), we joined the extracellular domain of the rat α6 subunit to the transmembrane and intracellular portion of the closely related rat α3 subunit. Alanine analogs were then tested against α3β2 or α6/α3β2β3 subunit combinations heterologously expressed in oocytes. The β3 subunit was used with α6/α3β2, for without it there was generally little or no functional expression. In addition, β3 is associated with native α6β2* -containing nAChRs (Zoli et al., 2002; Cui et al., 2003). Results are shown in FIG. 1 and Table 1.

TABLE 1

Activity of alanine-substituted MII analogs

| Toxin | Rat α3β2 IC$_{50}$ nM | Rat α6/α3β2β3 IC$_{50}$ nM | Ratio[a] |
|---|---|---|---|
| MII | 2.18 (1.24-3.81) | 0.39 (0.281-0.548) | 5.59 |
| MII[S4A] | 15.8 (7.03-35.3) | 0.733 (0.513-1.05) | 21.56 |
| MII[N5A] | >10,000 | 793 (566-1110) | >12.6 |
| MII[P6A] | 4,420 (1880-10,400) | 253 (172-372) | 17.5 |
| MII[V7A] | 4.46 (3.28-6.05) | 10.6 (8.01-14.0) | 0.421 |
| MII[H9A] | 59.0 (44.1-78.9) | 0.790 (0.558-1.12) | 74.7 |
| MII[L10A] | 1.47 (0.642-3.38) | 0.482 (0.232-1.00) | 3.05 |
| MII[E11A] | 8.72 (6.84-11.1) | 0.160 (0.135-0.189) | 54.5 |
| MII[H12A] | 4,660 (2420-9000) | 604 (256-1420) | 7.72 |
| MII[S13A] | 2.54 (1.92-3.35) | 0.659 (0.450-0.966) | 3.85 |
| MII[N14A] | 25.7 (17.0-38.9) | 1.06 (0.742-1.52) | 24.2 |
| MII[L15A] | 34.1 (19.4-59.9) | 0.917 (0.657-1.28) | 37.2 |

[a]IC$_{50}$ α3β2/IC$_{50}$ α6/α3/β2β3.
Numbers in parentheses are 95% confidence intervals.

Substitution of alanine for Asn5, Pro6, or His 12 resulted in substantially decreased activity compared with native MII at both a 6* and a 3* nAChRs, whereas substitution for Val7 had the most pronounced effect on the α6/α3,β2β3 nAChR. Substitution for Ser4, His9, Leu10, Glu11, Ser13, Asn14, and Leu15 had only modest effects on α6/α3β2, β3; however, mutations a Ser4, His9, Glu11, Asn14, and Leu15 resulted in substantially lower activity on α3, β2 nAChRs. Thus, these mutations are analogs that preferentially block α6/α3β2β3 versus α3β2 nAChRs. We note that for certain analogs, including S4A, L10A, E11A, S13A, and N14A, the $t_{1/2}$ for recovery from toxin block of α6/α3β2β3 nAChLRs was long (>25 min). For these analogs, 10- to 15-min toxin incubations were used to achieve maximum block at 10 nM concentration, and 20- to 35-min incubations were used to achieve maximum block at I nM concentration. A slow off-rate but similar affinity to other analogs implies that the analogs with a slow off-rate also have slower on-rates and thus the need for longer application times. MII[H9A] and MII[L15A] failed to block α4β2 nAChRs; at 10 μM peptide concentration, the ACh-evoked current was 105.8±2.4 and 102.3±5.3% of control, respectively (data from six oocytes).

Selectivity; of MII[E11A]: The single alanine substitution MII[E11A] has ~50-fold preference for α6/α3β2β3 versus α3β2 nAChRs and seems to be the most potent analog on α6/α3β2β3 nAChRs. We therefore tested its effects on additional nAChR subtypes. The apparent on-rate for α6/α3β4 nAChRs is slow; at concentrations of toxin ≦10 nM, 60 to 70 min of toxin application was required to reach a steady-state level of nAChR block. Concentration-response curves are shown in FIG. 2 and IC$_{50}$ values are shown in Table 2.

TABLE 2

Activity of MII[E11A]

| | IC$_{50}$ nM | 95% Confidence Interval | Ratio[a] |
|---|---|---|---|
| α2β2 | >10,000 | | >62,500 |
| α2β4 | >10,000 | | >62,500 |
| α3β2 | 8.72 | 6.84-11.1 | 54.5 |
| α3β4 | 2100 | 1330-3310 | 13,100 |
| α4β4 | >10,000 | | >62,500 |
| α6/α3β2 | 0.154 | 0.134-0.178 | 0.962 |
| α6/α3β2β3 | 0.160 | 0.135-0.189 | 1.00 |
| α6/α3β4 | 6.44 | 4.33-9.57 | 40.3 |
| α7 | 1051 | (731-1510) | 6,570 |

[a]nAChR subtype IC$_{50}$/α6/α3β2β3 IC$_{50}$

Figure 3A:
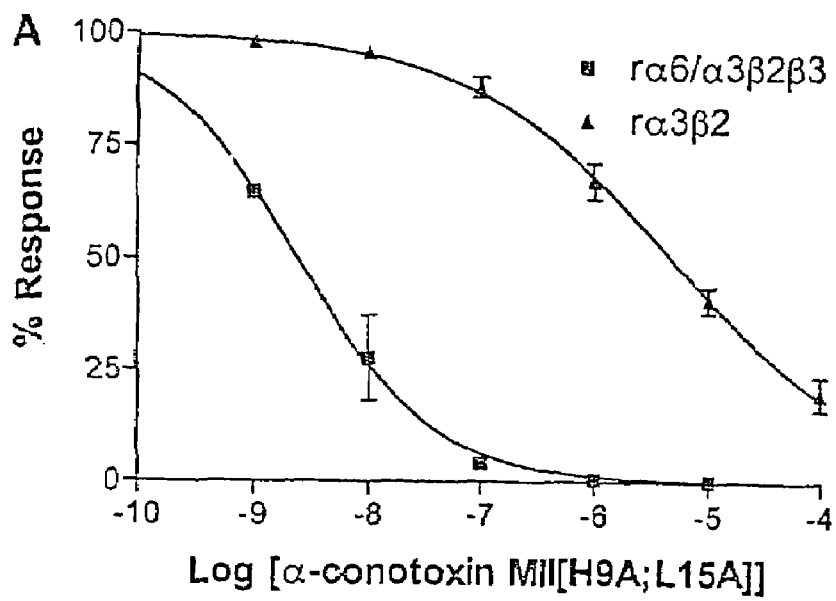
FIGS. 3A and 3B show that The [H9A,L15A] analog of α-MII discriminates between α6* and α3* nAChRs. (The * indicates the possible presence of additional subunits.) Peptide was applied to oocytes expressing the indicated nAChR subunit combinations as described in the Examples.
Figure 3B:
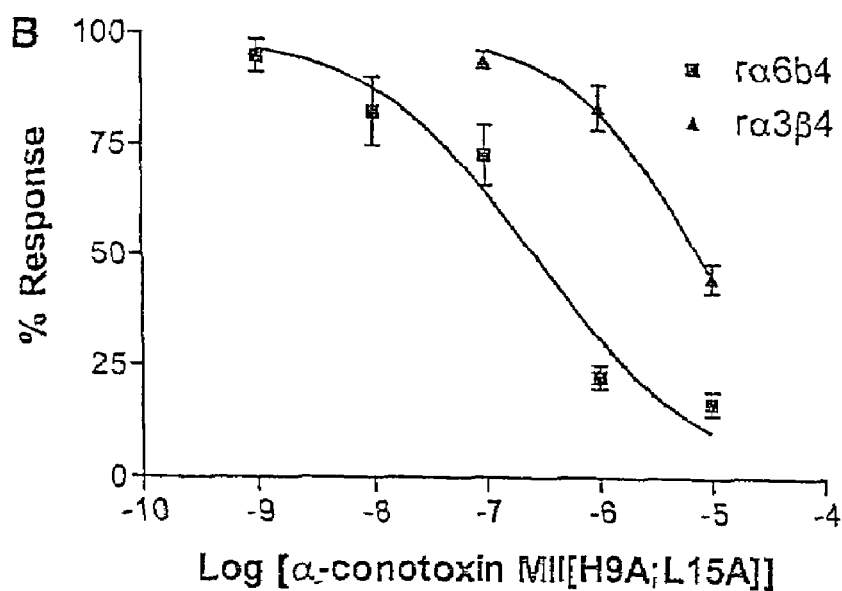

Double Mutants: A series of double alanine-substituted mutations was also constructed. These mutations were tested with respect to their activity at α6/α3β2β3 and α3β2 nAChRs. As seen in Table 3, each of these double mutants preferentially blocks the α6/α3β2β3 receptor versus the α3β2 receptor. The IC$_{50}$ of the MII[H9A;L15A] analog was approximately 2000-fold lower for α6/α3β2β3 versus α3β2, and this analog was selected for further characterization (FIG. 3).

TABLE 3

Activity of doubly substituted MII analogs

| Toxin | Rat α3β2 IC$_{50}$ nM | Rat α6/α3β2β3 IC$_{50}$ nM | Ratio[a] |
|---|---|---|---|
| MII[S4A; H9A] | 207 (156-274) | 1.97 (1.31-2.97) | 105 |
| MII[H9A; L15A] | 4850 (3540-6630) | 2.40 (1.68-3.43) | 2020 |
| MII[L10A; L15A] | 17.2 (8.11-36.6) | 1.80 (1.26-2.56) | 9.56 |

TABLE 3-continued

Activity of doubly substituted MII analogs

| Toxin | IC$_{50}$ | | Ratio[a] |
|---|---|---|---|
| | Rat α3β2 nM | Rat α6/α3β2β3 nM | |
| MII[E11A; L15A] | 50.1 (41.4-60.6) | 0.415 (0.223-0.772) | 121 |

[a]IC$_{50}$ α3β2/IC$_{50}$ α6/α3/β2β3.
Numbers in parentheses are 95% confidence intervals.

Figure 4:
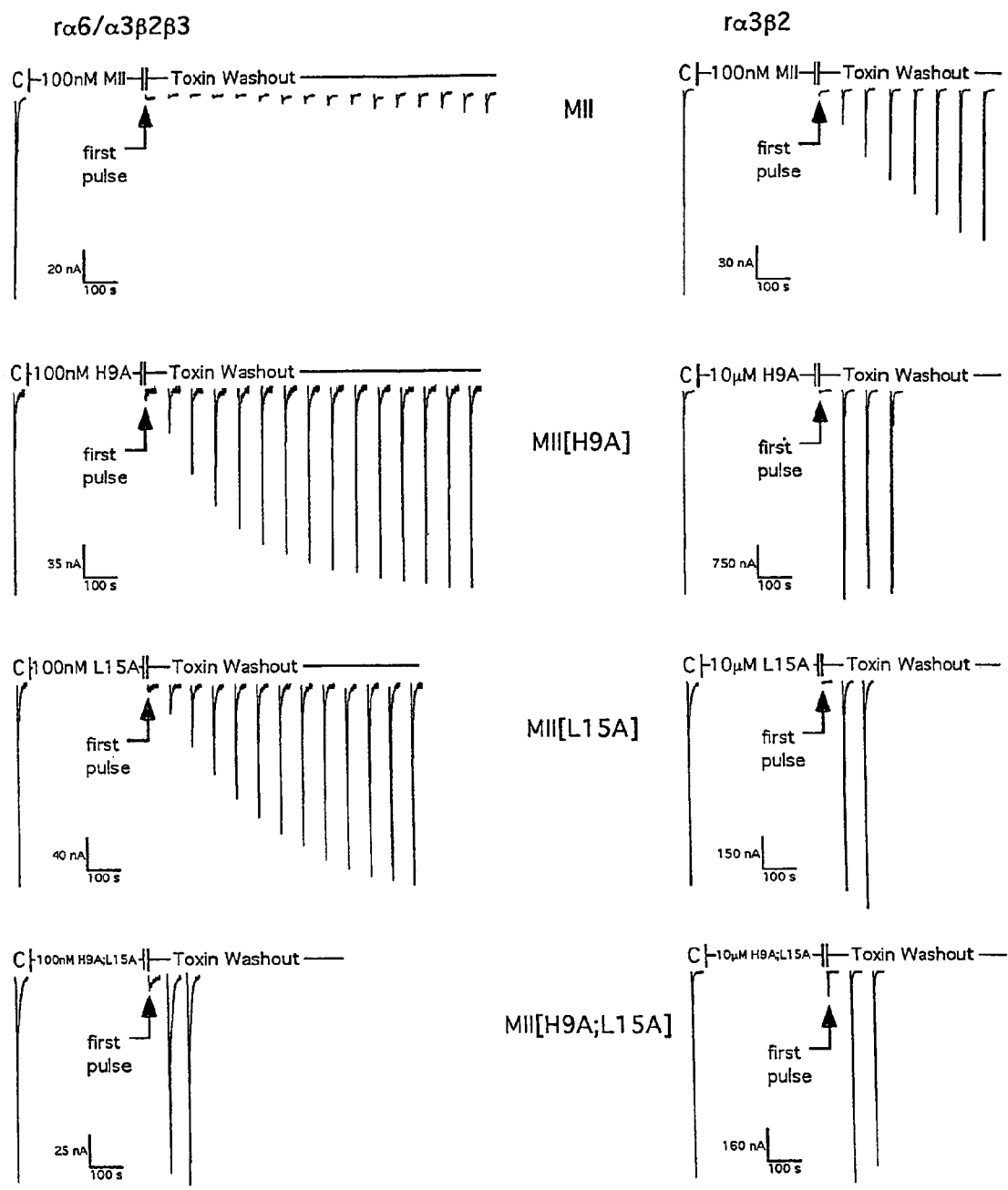
FIG. 4 shows the kinetics of block. MII, MII[H9A], MII [L15A], and MII[H9A;L15A] were applied to $X.$ $laevis$ oocytes heterologously expressing rat α6/α3β2β3 and α3β2 nAChRs. Peptide at the indicated concentrations was bath-applied for 5 min and then washed out. Kinetics of unblock were monitored by applying a 1-s pulse of ACh every 1 min.
Figure 5:
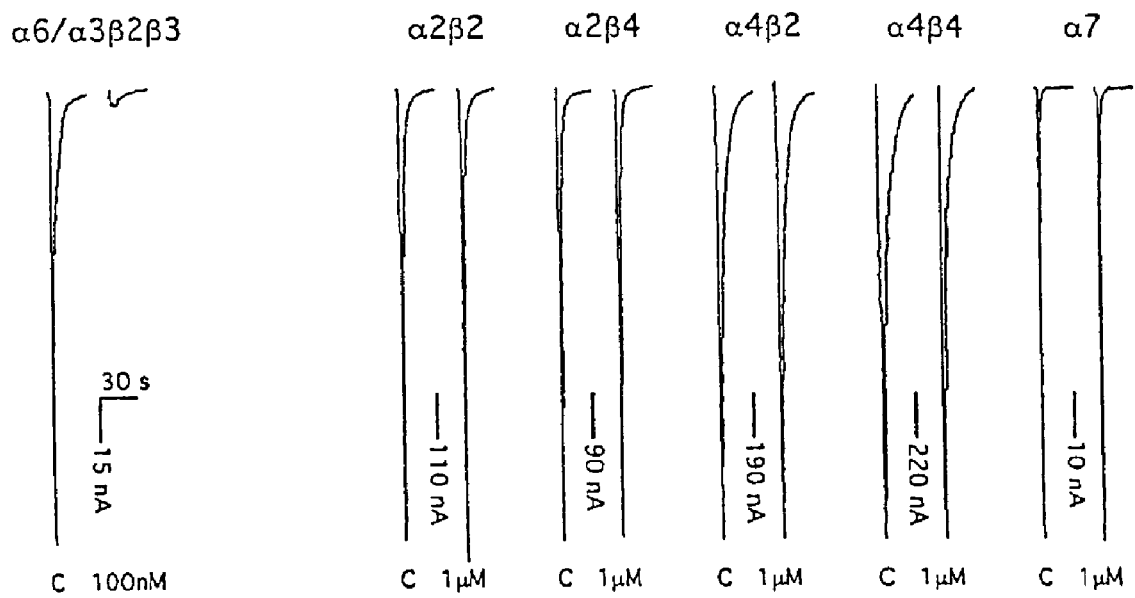
FIG. 5 shows the effects of MII[H9A,L15A] on additional nAChR subtypes. Peptide at 100 nM (α6/α3β2β3) and 1 μM (all other subtypes) was bath-applied for 5 min to $X.$ $laevis$ oocytes expressing the indicated rat nAChR subunits. Traces are representative of experiments on three to five oocytes. C, control response to ACh. Second response in each trace pair is the response to ACh in the presence of peptide.

Kinetics of Block by MII[H9A;L 15A]: α-Conotoxin MII is slowly reversible α3β2 nAChRs and very slowly reversible on α6/α3β2β3 nAChRs (FIG. 4). Substitution of Ala for His9 or Leu15 leads to more rapid recovery from block for both receptor subtypes. In the case of the double mutant MII[H9A; L15A] recovery from toxin block is rapid. The magnitude of the change of recovery rate is greater than the magnitude of change in IC$_{50}$ at the α6/α3β2β3 receptor. This implies that changes in the peptide that lead to a rapid off-rate also lead to a faster on-rate of binding. We note that α-conotoxin GIC, a more rapidly reversible homolog of α-conotoxin MII, also has an alanine rather than the histidine found in position 9 of α-MII (McIntosh et al., 2002). Activity of MII[H9A;L15A] on Other nAChR Subtypes: MII[H9A;L15A] has highest affinity for the α6/α3β2β3 subunit combination and ~100-fold less activity on the α6/α3β4 combination (FIG. 3). MII [H9A;L15A] has low or no activity on the remaining neuronal subunit combinations tested, including α2β2, α2β4, α3β4, α4β2, α4β4, and α7 (FIG. 5 and Table 4). Thus MII[H9A; L15A] selectively blocks α6* nAChRs, with preference for the α6/α3β2β3versus α6/α3β4 subunit combination.

TABLE 4

Effects of MII[H9A; L15A]

| Receptor | Concentration of MII[H9A; L15A] | |
|---|---|---|
| | 10 μM | 1 μM |
| Rα2β2 | 102 ± 1.4 | 103 ± 1.9 |
| Rα2β4 | 96.7 ± 3.2 | 95.9 ± 2.3 |
| Rα4β2 | 98.5 ± 4.4 | 101 ± 2.5 |
| Rα4β4 | 99.0 ± 4.0 | 100 ± 5.6 |
| Rα7 | 61.4 ± 2.3 | 100 ± 1.5 |

Values are the percentage of control ± S.E.M.

Effect of β3 Subunit: Occasional expression of α6/α3β2 was seen without coinjection of the β3 subunit. MII[H9A; L15A] blocked α6/α3β2 nAChRs with an IC$_{50}$ of 8.21 (6.36-10.6) nM compared with 2.4 nM (1.68-3.43) for α6/α3β2β3. As indicated above (FIG. 2 and Table MII[E11A] blocked α6/α3β2 nAChRs with an IC$_{50}$ of 0.154 nM (0.134-0.178) compared with 0.16 nM (0.135-0.189) on α6/α3β2β3 nAChRs. Numbers in parentheses are 95% confidence intervals.

Figure 6:
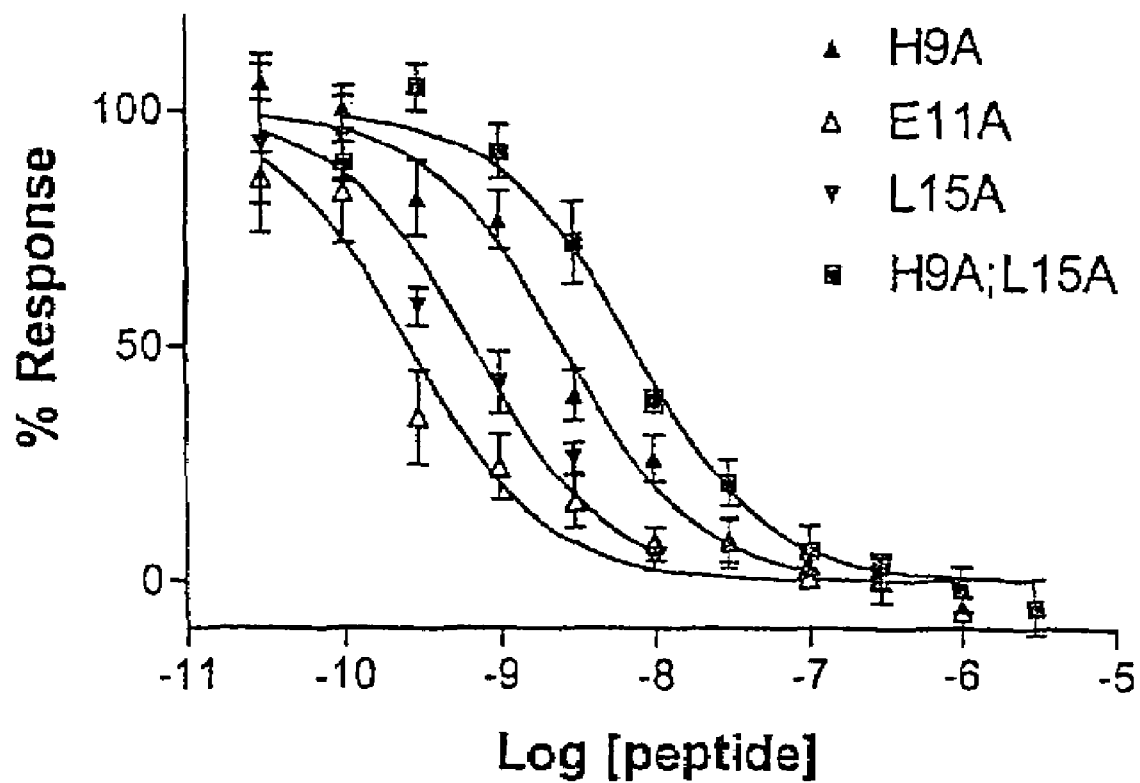
FIG. 6 shows the concentration-response analysis of α-conotoxin MII analogs on native nAChRs. Analogs were assessed for their ability to displace $[I^{125}I]$α-conotoxin MII binding on mouse brain homogenates as described in the Examples. Nonspecific binding was defined with 1 μM epibatidine. $K_i$ values are shown in Table 5. The Hill slope was 0.95±0.13, 0.89±0.14, and 1.1±0.14 for MII[H9A], MII [L15A], and MII[H9A;L15A], respectively. ±values are standard error of the mean. Data are from three to seven experiments.

Activity of Analogs at Native Moutse Brain nAChRs: A concentration-response analysis was performed on four of the analogs with α6/α3* versus α3* selectivity—MII[H9A], MII [E11A], MII[L15A], and MII[H9A;L15A]—using inhibition of [$^{125}$I]α-conotoxin MII binding (Whiteaker et al., 2000b) to mouse brain homogenates. Results are shown in FIG. 6. The values obtained for these analogs correlate well with values obtained on α6/α3β2β3 rather than α3β2 nAChRs as expressed in X laevis oocytes (Table 5).

TABLE 5

α-Conotoxin MII and analogs

| Peptide | IC$_{50}$ Rat α3β2 | IC$_{50}$ Rat α6/α3β2β3 nM | K$_i$ Mouse CNS α-MII Site |
|---|---|---|---|
| α-MII | 2.2 (1.2-3.8) | 0.39 (0.28-0.55) | 0.22 (0.20-0.25) |
| MII[H9A] | 59 (44-79) | 0.79 (0.56-1.1) | 1.1 (0.84-1.6) |
| MII [E11A] | 8.7 (6.8-11.1) | 0.16 (0.13-0.19) | 0.27 (0.19-0.37) |
| MII [L15A] | 34 (19-60) | 0.92 (0.65-1.3) | 0.30 (0.21-0.45) |
| MII[H9A; L15A] | 4800 (3500-6600) | 2.4 (1.7-3.4) | 3.3 (2.5-4.3) |

Rat nAChRs were heterologously expressed in oocytes, and functional block of ACh-induced current was measured. Radioiodinated α-conotoxin MII was used with mouse brain homogenates to examine the competition binding of the indicated peptides. See FIGS. 1, 2, 3, and 6.
Numbers in parentheses are 95% confidence intervals.

Example 3

Discussion

Although the sequence of the coding region for the α6 gene has been known for many years (Lamar et al., 1990), its functional significance has been challenging to elucidate because of difficulties in heterologously expressing α6 and because of a lack of subtype-specific ligands. Indeed, originally it was not entirely certain that the α6 gene encoded a nicotinic receptor subunit. The α6 subunit has relatively discrete localization, with expression in catacholaminergic nuclei including the locus coeruleus, the ventral tegmental area, and the substantia nigra (Le Novèere et al., 1996; Göldner et al., 1997; Han et al., 2000; Quik et al., 2000; Azam et al., 2002). It is also found in trigeminal ganglion and olfactory bulb (Keiger and Walker, 2000). In addition, α6 complexes have been reported in chick retina (Vailati et al., 1999). The α6 mRNA expression pattern overlaps extensively with that of the α3 subunit, leading to initial confusion over the composition of [$^{125}$I]α-conotoxin MII-binding nAChRs (Whiteaker et al., 2000b).

Subunit-specific antibodies have been used to immunoprecipitate α6* receptors from chick retina. When reconstituted in lipid bilayers, these receptors formed cationic channels characteristic of nAChRs, thus establishing a functional role for native α6* nAChRs (Vailati et al., 1999). Antibodies have also been used recently to demonstrate the presence of α6β2* nAChRs in striatal dopaminergic terminals in rat. β03 and/or α4 subunits are also present in a proportion of these nAChRs (Zoli et al., 2002). Subunit knockout mice suggest that the high-affinity binding site of [$^{125}$I]α-conotoxin MII is predominately composed of α6* rather than α3* nAChRs (Champtiatix et al., 2002; Whiteaker et al., 2002). It has been hypothesized recently that putative α6* nAChRs in the striatum may participate in the pathophysiology of Parkinson's disease, a neurodegenerative disorder characterized by progressive loss of dopamine neurons. Treatment of primates with 1-methyl-4-phenyl-1,2,3,6-tetrahydropyridine (a dopaminergic neurotoxin) leads to selective decline of putative α6β2* nAChRs (Quik et al., 2001; Kulak et al., 2002). Thus, there is a significant need for ligands that selectively act at α6* nAChRs.

We demonstrate in this report that certain analogs of α-conotoxin MII exhibit preferential loss of activity at α3β2 versus α6/α3β2β3 nAChRs. Additionally, at concentrations tested, the MII[H9A;L15A] analog has little or no activity at α2*, α4*, or 7* nAChRs. Indeed, MII[H9A;L15A] is the most selective α6 ligand thus far reported.

A number of native α-conotoxins have been characterized that target various subtypes of nAChRs. Despite their differences in primary sequence, NMR and X-ray crystallography studies show a high conservation of the structural peptide backbone (Hu et al., 1996, 1997, 1998; Shon et al., 1997; Hill et al., 1998; Cho et al., 2000; Park et al., 2001; Nicke et al., 2003). It seems that this backbone serves as a scaffold that presents a variety of amino acid side chains leading to differences in specificity. In the present study, we have systematically replaced the noncysteine residues of α-conotoxin MII with alanine. The predominant effect is to preferentially decrease activity at the α3β2 receptor relative to the α6/α3Γ2 (±β3) subunit combination.

In an attempt to further increase selectivity, double mutations were constructed from the more selective single mutation analogs. Each of these double mutants retains a low nanomolar $IC_{50}$ for the α6/α3β2β3 nAChR (Table 3). It is particularly noteworthy that the native MII peptide potently blocks both α6/α3β2β3 and α3β2 nAChRs, whereas the MII [H9A;L15A] analog discriminates between these nAChRs by three orders of magnitude. This discrimination is caused by differences in the extracellular region of the αsubunit because the transmembrane and intracellular portions of the chimeric α6/α3 and α3 subunits are identical. Also, the addition of the β3 subunit to α6/α3β2 nAChRs has only a 3.4-fold effect on MII[H9A,L15A] block. MII[E11A] also preferentially blocks α6/α3β2 versus α3β2 nAChRs, again implicating the extracellular portion of the α6 subunit. Furthermore, coexpression of the β3 subunit with the α6/α3 and β12 subunits had no effect on the $IC_{50}$ of MII[E11A]. However, the presence of a β2 versus β4 subunit does seem to influence peptide affinity. MII[E11A] preferentially blocks α6/α3β2 versus α6/α3β4 nAChRs and preferentially blocks α3β2 versus α3β4 nAChRs.

We used cloned rat receptor subunits heterologously expressed in X laevis oocytes to examine the differences between α3* and x6* nAChRs. Although difficult, occasional expression of α6 with either β2 or β4 subunits has been described. This expression is enhanced with the addition of the β3 subunit (Kuryatov et al., 2000+). Improved efficiency of expression has been achieved by combining the extracellular (putative ligand binding) domain of α6 with the remaining portion of either the α3 or α4 subunit (Kuryatov et al., 2000). We have exploited this technique to screen analogs of α6-conotoxin MII. It is possible that there are important differences between this chimeric receptor expressed in oocytes and native nAChRs. To assess this, the α-conotoxin MII analogs were also tested in a radioligand binding assay using native nAChR populations. As can be seen in Table 5, the analogs that potently block the rat α6/α3β2β3 nAChR heterologously expressed in oocytes also potently block the native mouse striatal nAChR bound by radiolabeled MII. This native receptor has been shown in previous studies to contain α6 (rather than α3) and β2 subunits (Champtiaux et al., 2002; Whiteaker et al., 2002; Zoli et al., 2002). Thus, the analogs have high affinity for both native and heterologously expressed α6β2* nAChRs. The H9A;L15A analog of MII also has a relatively high $IC_{50}$ for other nAChRs, including α2β2, α2β4, α3β2, α3β2, α4β2, α4β2, α4β4, and α7. Thus, this peptide represents a novel selective probe for discriminating among numerous nAChR subunit combinations.

The precise mechanism by which the [H9A] and [L15A] mutations cause a selective loss of affinity at α3β2 relative to α6/α3β2* nAChRs is not addressed by these studies. It has been determined that Lys185 and Ile188 of the α3 subunit are critically important for α-conotoxin MII binding to α3β2 nAChRs (Harvey et al., 1997), and these residues are conserved between the α3 and α6 subunits. The most facile explanation of the results presented here is that the crucial interactions between α-conotoxin MII and the α6 subunit may occur at other subunit side chains. Interestingly, both α-conotoxin PnIA and α-conotoxin MII interact with Ile188 but differ in other important interactions with the α3 subunit. α3 subunit Lys 185 is not essential to α-conotoxin PnIA binding, whereas Pro182 and Gln198 are (Everhart et al., 2003). Perhaps significantly, the latter two residues are not conserved between the α3 and α6 subunit. Because all of the above residues are found in the putative "C" loop of the α-subunit, it seems possible that interaction in this region may be of particular importance. However, several examples indicate that a more complex explanation may be needed. For instance, α-conotoxin PnIA and its derivative α-conotoxin PnIA[A10L] stabilize different states of the same nAChR (.Hogg et al., 2003), presumably by interacting with different sets of subunit residues, whereas α-conotoxin MI has been shown to interact in a different orientation with the same α subunit residues, depending on whether it is binding at an α/γ or α/δinterface (Sugiyama et al., 1998). These and a series of mutant-cycle analysis studies (Quiram et al., 1999, 2000; Bren and Sine, 2000) have indicated that toxin/channel interactions may be anchored by a small number of relatively strong interactions and supported by a large number of weaker interactions that strongly determine subtype selectivity (Rogers et al., 2000). If this more multifaceted model is correct, the maintenance of affinity between α-conotoxin MII [H9A;L15A] and the α6/α3β2* nAChR may reflect either a more prominent role of the "supporting" interactions with the native toxin than is seen for α3β2, which is retained after alteration of the His9 and Leu15 side chains.

Alternatively, the orientation of the toxin within the binding pocket may shift after substitution at the His9 and Leu15 positions, but the structure of the α6/α3 binding pocket may be better able to accommodate the new positioning than its α3 counterpart. The fact that several of the alanine mutants exhibit affinities similar to each other and native α-conotoxin MII but have radically different binding kinetics reinforces the idea that different interactions may stabilize the nAChR/toxin complex in each case. It seems likely that an accurate understanding of how the [H9A] and [L15A] mutations produce selectivity between α3β2 and α6/α3β2* nAChRs will require the performance of a comprehensive set of double mutant-cycle analyses.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

BIBLIOGRAPHY

Abiko, H. et al. (1986). *Brain Res.* 38:328-335.
Aldrete, J. A. et al. (1979). *Crit. Care Med.* 7:466-470.
Azam, L. et al. (2002). Expression of neuronal nicotinic acetylcholine receptor subunit mRNAs within midbrain dopamine neurons. *J Comp Neurol* 444: 260-274.
Barnay, G. et al. (2000). *J Med. Chest*.
Bitan, G. et al. (1997). *J. Peptide Res.* 49:421-426.
Bliss, et al. (1993). *Nature* 361:31.
Bodansky, et al. (1966). *Chem. Ind.* 38:1597-98.

Boring, et al. (993). *Can Cancer J. Clin.* 43:7.

Bormann, J. (1989). *Euro. J. Pharmacol.* 166:591-592.

Brauner-Osborne, H. et al. (2000). *J. Medicinal Chem.* 43:2609-2645.

Bren, N. and Sine, S. M. (2000). Hydrophobic pairwise interactions stabilize α-conotoxin MI in the muscle acetylcholine receptor binding site. *J Biol Chem* 275: 12692-12700.

Cartier, G. E. et al. (1996). A new α-conotoxin which targets α3β2 nicotinic acetylcholine receptors. *J Biol Chem* 271: 7522-7528. Cavalheiro, E. A. et al. (2001). *Proc. Natl. Acad. Sci. USA* 98:5947-5948.

Champtiaux, N. et al. (2002). Distribution and pharmacology of α6-containing nicotinic acetylcholine receptors analysed with mutant mice. *J Neurosci* 22: 1208-1217.

Chandler, P. et al. (1993). *J. Biol. Chest.* 268:17173-17178.

Changeux, J-P. (1993). Chemical signaling in the brain. *Scientific American* 269: 58-62.

Chaplan S. R. (1997). *J Pharmacol. Exp. Ther.* 280:829-838.

Cheng, Y. C. and Prusoff, W. H. (1973). Relationship between the inhibition constant ($K_i$) and the concentration of inhibitor which causes 50% inhibition ($IC_{50}$) of an enzymatic reaction. *Biochem Pharmacol* 22: 3090-3108.

Cho, J. H. et al. (2000). Nuclear magnetic resonance solution conformation of α-conotoxin AuIB, an α3β4 subtype-selective nicotinic acetylcholine receptor antagonist. *J Biol Chem* 275: 8680-8685.

Codere, T. J. (1993). *Eur. J Neurosci.* 5:390-393.

Corringer, P. J. et al. (2000). Nicotinic receptors at the amino acid level. *Annu Rev Pharmacol Toxicol* 40: 431-458.

Craik, D. J. et al. (1991). *Toxicon* 39:43-60.

Cui, C. et al. (2003). The β3 nicotinic receptor subunit: a component of α-conotoxin MII binding nAChRs which modulate dopamine release and related behaviors. *J Neurosci* 23: 11045-11053.

Deneris, E. S. et al. (1989). Beta 3: A new member of the nicotinic acetylcholine receptor gene family is expressed in the brain. *J Biol Chem* 264: 6268-6272.

Dorr et al. (1994). Cancer Chemotherapy Handbook, 2d Ed., pp. 15-34, Appleton & Lange, Conn.

Ettinger, L. J. et al. (1978). *Cancer* 41:1270-1273.

Everhart, D. et al. (2003). Identification of residues that confer α-conotoxin PIA sensitivity on the α3 subunit of neuronal nicotinic acetylcholine receptors. *J Pharmacol Exp Ther* 306: 665-670.

Gööldner, F. M. et al. (1997). Immunohistochemical localization of the nicotinic acetylcholine receptor subunit α6 to dopaminergic neurons in the substanitia nigra and ventral tegmental area. *Neuroreport* 8: 2739-2742.

Greenamyre, J. T. and O'Brien, C. F. (1991). *Arch. Neurol.* 48:977-981.

Han, Z-Y. et al. (2000). Localization of nAChR subunit mRNAs in the brain of *Macaca mulatta*. *Eur J Neurosci* 12: 3664-3674.

Harvey, S. C. et al. (1997). Determinants of specificity for α-conotoxin MII on α3β2 neuronal nicotinic receptors. *Mol Pharmacol* 51: 336-342.

Heyes, M. P., et al. (1989). *Ann. Neurol.* 26: 275-277.

Hill, J. M. et al. (1998). Three-dimensional solution structure of α-conotoxin MII by NMR spectroscopy: effects of solution environment on helicity. *Biochemistry* 37: 15621-15630.

Hogg, R. C. et al. (2003). α-Conotoxin PnIA and [A10L] PnIA stabilize different states of the α7-L247T nicotinic acetylcholine receptor. *J Biol Chem* 278: 26908-26914.

Horiki, K. et al. (1978). *Chemistry Letters* 165-68.

Hu, S-H. et al. (1997). Crystal structure at 1.1 Å resolution of α-conotoxin PnIB: comparison with α-conotoxins PnIA and GI. *Biochemistry* 36: 11323-11330.

Hu, S-H. et al. (1996). The 1.1 Å crystal structure of the neuronal acetylcholine receptor antagonist, α-conotoxin PnIA from *Conus pennaceus*. *Structure* 4: 417-423.

Hu, S-H. et al. (1998). The 1.1 Å resolution crystal structure of [Tyr15]EpI, a novel α-conotoxin from *Conus episcopatus*, solved by direct methods. *Biochemistry* 37: 11425-11433.

Hubry, V. et al. (1994). *Reactive Polymers* 22:231-241.

Hunter(1991). Cell64:249.

Johnson et al. (1990). *Ann. Rev. Pharmacol. Toxicol.* 30:707-750.

Kaiser et al. (1970). *Anal. Biochem.* 34:595.

Kapoor (1970). *J Pharm. Sci.* 59:1-27.

Keiger, C. J. and Walker, J. C. (2000). Individual variation in the expression profiles of nicotinic receptors in olfactory bulb and trigeminal ganglion and identification of α2, α6, α9 and β03 transcripts. *Biochem Pharmacol* 59: 233-240.

Kornreich, W. D. et al. (1986). U.S. Pat. No. 4,569,967.

Kulak, J. M. et al. (2002). Loss of nicotinic receptors in monkey striatum after 1-methyl-4-phenyl-1,2,3,6-tetrahydropyridine treatment is due to a decline in α-conotoxin MII sites. *Mol Pharmacol* 61: 230-238.

Kuryatov, A. et al. (2000). Human α6 AChR subtypes: subunit composition, assembly and pharmacological responses. *Neuropharmacology* 39: 2570-2590.

Lamar, D. et al. (1990). Amplification of genomic sequences identified in new gene, α6, in the nicotinic acetylcholine receptor gene family. *Soc Neurosci Abstr* 16: 2852.

Land et al. (1983). *Science* 222:771.

Le Novére, N. et al. (1996). Neuronal nicotinic receptor α6 subunit mRNA is selectively concentrated in catecholaminergic nuclei of the rat brain. *Eur J Neurosci* 8: 2428-2439.

Le Novéere, N. et al. (1999). Involvement of α7 nicotinic receptor subunit in nicotine-elicited locomotion, demonstrated by in vivo antisense oligonucleotide infusion. *Neuroreport* 10: 2497-2501.

Lipton, S. A. (1991). *Neuron* 7:111-118.

Lipton, S. A. (1994). *Dav Neurosci.* 61:145-15 1.

Lipton, S. A. (1996). *Brain Pathol* 6:507-517.

Liu, H. et al. (1997). *Nature* 386:721-724.

Luer, M. S. Hatton, J. (1993). *Annals Pharmcotherapy* 27:912-921.

Luo, S. et al. (1998). α-Conotoxin AuIB selectively blocks α3β4 nicotinic acetylcholine receptors and nicotine-evoked norepinephrine release. *J Neurosci* 18: 8571-8579.

Luo, S. et al. (1999). Single-residue alteration in α-conotoxin PnIA switches its nAChR subtype selectivity. *Biochemistry* 38: 14542-14548.

Luo, Z. et al. (1994). Regulation of acetylcholinesterase mRNA stability by calcium during differentiation from myoblasts to myotubes. *J Biol Chem* 269: 27216-27223.

McIntosh, J. M. et al. (1998). *Methods Enzymol.* 294:605-624.

McIntosh, J. M. et al. (2002). α-Conotoxin GIC from *Conus geographus*, a novel peptide antagonist of nAChRs. *J Biol Chem* 277: 33610-33615.

*The Merck Manual of Diagnosis and Therapy*, 16 Ed., Berkow, R. et al., eds., Merck Research Laboratories, Rahway, N.J., pp. 1436-1445 (1992).

*Methoden der Organischen Chemie* (Houben-Weyl): *Synthese von Peptiden*, E. Wunsch (Ed.), Georg Thieme Verlag, Stuttgart, Ger. (1974).

Muller, W. E. et al. (1996). *Prog Mol Subcell Biol.* 16:44-57.

Nehlig, A. et al. (1990). Effects of phenobarbital in the developing rat brain. In *Neonatal Seizures*, Wasterlain, C. G. and Vertt, P. (eds.), Raven Press, New York, pp. 285-194.

Nicke, A. et al. (2003). Isolation, structure and activity of GID, a novel 4/7α-conotoxin with an extended N-terminal sequence. *J Biol Chem* 278: 3137-3144.

Nishida, K. et al. (1996). *J Neurochem* 66:433-435.

Nishiuchi, Y. et al. (1993). *Int. J. Pept. Protein Res.* 42:533-538.

Okarvi, S. M. (2001). *Eur. J. Nucl. Med* 28:929-938.

Olney, J. W. et al. (1987). *Eur. J. Pharmacol.* 142:319-320.

Olivera, B. M. et al. (1985). *Science* 230:1338-1343.

Olivera, B. M. et al. (1990). *Science* 249:257-263.

Olivera, B. M. et al. (1996). U.S. Pat. No. 5,514,774.

Ornstein, et al. (1993). *Biorganic Medicinal Chemistry Letters* 3:43-48.

Park, K. H. et al. (2001). Solution conformation of α-conotoxin EI, a neuromuscular toxin specific for the α1/δsubunit interface of Torpedo nicotinic acetylcholine receptor. *J Biol Chem* 276: 49028-49033.

Popik, P. et al. (1995). *Pharmacol. Rev.* 47:235-253.

Quik, M. et al. (2000). Localization of nicotinic receptor subunit mRNAs in monkey brain by in situ hybridization. *J Comp Neurol* 424: 58-69.

Quik, M. et al. (2001). Vulnerability of $^{125}$I-α-conotoxin MII binding sites to nigrostriatal damage in monkeys. *J Neurosci* 21: 5494-5500.

Quiram, P. A. et al. (1999). Pairwise interactions between neuronal α7 acetylcholine receptors and α-conotoxin ImI. *J Biol Chem* 274: 19517-19524.

Quiram, P. A. et al. (2000). Pairwise interactions between neuronal α7 acetylcholine receptors and α-conotoxin PnIB. *J Biol Chem* 275: 4889-4896.

Raber, J. et al. (1996). *Virology* 226:362-373.

Rall, T. W. and Schleifer, L. S. in *Goodman and Gilman's The Pharmacological Basis of Therapeutics*, Seventh Ed., Gilman, A. G. et al., eds., Macmillan Publishing Co., New York, pp. 446-472 (1985).

*Remington's Pharmaceutical Sciences*, 18th Ed. (1990, Mack Publishing Co., Easton, Pa.).

Rivier, J. R. et al. (1978). *Biopolymers* 17:1927-38.

Rivier, J. R. et al. (1987). *Biochem.* 26:8508-8512.

Rogers, J. P. et al. (2000). Structure-activity relationships in a peptide α7 nicotinic acetylcholine receptor antagonist. *J Mol Biol* 304: 911-926.

Ruley (1983). *Nature* 304:602.;

Rytik, P. G. et al. (1991). Anti-HIV activity of memantine. *AIDS Res Hum Retrovir* 7:89-95.

Rzeski, W. et al. (2001). *Proc. Natl. Acad. Sci. USA* 98:6372-6377.

Sambrook, J. et al. (1989). *Molecular Cloning: A Laboratory Manual*, 2nd Ed., Cold Spring Harbor Laboratory, Cold Spring Harbor, N.Y.

Shon, K. et al. (1997). Three-dimensional solution structure of α-conotoxin MII, an α3β2 neuronal nicotinic acetylcholine receptor-targeted ligand. *Biochemistry* 36: 15693-15700.

Schroder & Lubke (1965). *The Peptides* 1:72-75, Academic Press, NY.

Sei, Y. et al. (1996). *J Neurochem.* 66:296-302.

Skolnick, P. et al. (1992). *J. Neurochem.* 59:1526-1521.

Spanagel, R. and Zieglgansberger, W. (1997). *Trends Pharmacol. Sci.* 18:54-59.

Starr, M. S. (1995). *J. Neural Tans.[P-D Sect]* 10:141-185.

Stewart and Young, *Solid-Phase Peptide Synthesis*, Freeman & Co., San Francisco, Calif. (1969).

Sugiyama, N. et al. (1998). Residues at the subunit interfaces of the nicotinic acetylcholine receptor that contribute to α-conotoxin MI binding. *Mol Pharmacol* 53: 787-794.

Sweetman, P. M. (1993). *Eur. J. Neurosci.* 5:276-283.

Takano, T. et al. (2001). *Nature med* 7:1010-1015.

Troupini, A. S. et al. (1986). MK-801. In *New Anticonvulsant Drugs, Current Problems in Epilepsy* 4, Meldrum, B. S. and Porter, R. J. (eds.), John Libbey, London, pp. 191-202.

Trujillo, K. A. and Akil, H (1995). *Drug Alcohol Depend.* 38:139-154.

Ungerstedt, U. et al. (1973). Animal Models of Parkinsonism. In *Advances in Neurology: Progress in the Treatment of Parkinsonism*, Calne, D. B., Ed., Raven Press, New York, pp 257-271.

Vailati, S. et al. (1999). Functional α6-containing nicotinic receptors are present in chick retina. *Mol Pharmacol* 56: 11-19.

Vale et al. (1978). U.S. Pat. No. 4,105,603.

Van de Steen, P. et al. (1998). *Critical Rev. in Biochemn. and Mol. Biol.* 33:151-208.

Virgolini, I. et al. (2001). *J Nucl Med* 45:153-9.

White, H. S., et al. (1992). *Epilepsy Res.* 12:217-226.

White, H. S., et al. (1995). Experimental Selection, Quantification, and Evaluation of Antiepileptic Drugs. In *Antiepileptic Drugs*, 4th Ed., Levy, R. H., eds., Raven Press, N.Y., pp. 99-110.

Whiteaker, P. et al. (2000a). Identification of a novel nicotinic binding site in mouse brain using [$^{125}$I]-epibatidine. *Br J Pharmacol* 131: 729-739.

Whiteaker, P. et al. (2000b). $^{125}$I-α-Conotoxin MII identifies a novel nicotinic acetylcholine receptor population in mouse brain. *Mol Pharmacol* 57: 913-925.

Whiteaker, P. et al. (2002). The role of the α3 subunit in neuronal nicotinic binding populations. *J Neurosci* 22: 2522-2529.

Wittekindt, B. et al. (2001). *Neuropharmacol* 41:753-761.

Wong, E. H. P. et al. (1986). *Proc. Natl. Acad. Sci. USA* 83:7104-7108.

Zhou L. M., et al. (1996). *J. Neurochem.* 66:620-628.

Zigmond, M. J. et al. (1987). Parkinsonism: Insights from animal models utilizing neurotoxic agents. In *Animal Models of Demential*, Coyle, J. T., Ed., Alan R. Liss, Inc., pp 1-38.

Zimm, S. et al. (1984). *Cancer Res.* 44:1698-1701.

Zoli, M. et al. (2002). Identification of the nicotinic receptor subtypes expressed oil dopaminergic terminals in the rat striatum. *J Neurosci* 22: 8785-8789.

U.S. Pat. No. 5,550,050 (1996).

U.S. Pat. No. 5,844,077 (1998).

Published PCT Application WO 92/19195 (1992).

Published PCT Application WO 94/25503 (1994).

Published PCT Application WO 95/01203 (1995).

Published PCT Application WO 95/05452 (1995).

Published PCT Application WO 96/02286 (1996).

Published PCT Application WO 96/02646 (1996).

Published PCT Application WO 96/40871 (1996).

Published PCT Application WO 96/40959 (1996).

Published PCT Application WO 97/12635 (1997).

Published PCT Application WO 98/03189 (1998).

PCT Published Application WO 00/23092 (2000).

What is claimed is:

1. An isolated conopeptide selected from the group consisting of:
   (a) a conopeptide having the amino acid sequence Gly-Cys-Cys-Ser-Asn-Pro-Val-Cys-His-Leu-Ala-His-Ser-Asn-Leu-Cys (SEQ ID NO:8);
   (b) a derivative of (a) having α6-containing nicotinic acetylcholine receptor binding activity, wherein the derivative is a peptide in which the Pro residue is substituted with hydroxy-Pro or O-glycosylated hydroxy-Pro; one or both of the Ser residues is or are substituted with O-glycosylated Ser; one or both of the Asn residues is or are substituted with N-glycosylated Asn; the Cys residues are in D or L configuration; or one or more of the Cys residues is or are substituted with homocysteine in the D or L configuration; and
   (c) a physiologically acceptable salt of (a) or (b).

2. A pharmaceutical composition comprising the conopeptide of claim 1 and a pharmaceutically acceptable carrier.

3. The isolated conopeptide of claim 1 which is the peptide of SEQ ID NO:8.

* * * * *